US008993537B2

(12) United States Patent
Yue et al.

(10) Patent No.: US 8,993,537 B2
(45) Date of Patent: Mar. 31, 2015

(54) FORMING POROUS SCAFFOLD FROM CELLULOSE DERIVATIVES

(75) Inventors: Zhilian Yue, Singapore (SG); Feng Wen, Singapore (SG); Hanry Yu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 80 days.

(21) Appl. No.: 13/611,339

(22) Filed: Sep. 12, 2012

(65) Prior Publication Data
US 2013/0005945 A1 Jan. 3, 2013

Related U.S. Application Data

(60) Division of application No. 12/824,105, filed on Jun. 25, 2010, now Pat. No. 8,283,028, which is a continuation-in-part of application No. 12/809,534, filed as application No. PCT/SG2008/000491 on Dec. 18, 2008, now abandoned.

(60) Provisional application No. 61/006,090, filed on Dec. 18, 2007.

(51) Int. Cl.
| A61K 31/717 | (2006.01) |
| A61L 27/20 | (2006.01) |
| A61L 27/56 | (2006.01) |
| C08B 11/20 | (2006.01) |
| C08J 9/28 | (2006.01) |
| C08L 1/14 | (2006.01) |

(52) U.S. Cl.
CPC ............. *A61L 27/20* (2013.01); *A61L 27/56* (2013.01); *C08B 11/20* (2013.01); *C08J 9/28* (2013.01); *C08L 1/14* (2013.01); *C08J 2201/024* (2013.01); *C08J 2201/0484* (2013.01); *C08J 2207/10* (2013.01); *C08J 2301/28* (2013.01)
USPC .............................. 514/54; 514/57; 536/124

(58) Field of Classification Search
CPC .................................................. A61K 31/717
USPC ....................................................... 514/57, 54
See application file for complete search history.

(56) References Cited

U.S. PATENT DOCUMENTS

| 4,964,989 A | 10/1990 | Gsell |
| 5,151,217 A | 9/1992 | Price |

FOREIGN PATENT DOCUMENTS

| JP | H0338428 A | 2/1991 |
| WO | 95/31500 A2 | 11/1995 |
| WO | 00/78553 A1 | 12/2000 |
| WO | 02/074158 A2 | 9/2002 |
| WO | WO 02074158 A2 * | 9/2002 |
| WO | 03/022910 A1 | 3/2003 |

OTHER PUBLICATIONS

Office Action (Notice of Reasons for Rejection), dated Jul. 8, 2013, issued in related Japanese Application No. 2010-539393.
International Search Report and Written Opinion, mailed Apr. 1, 2009, in related PCT patent application No. PCT/SG2008/000491.
Andrews et al., "Rheological characterisation of primary and binary interactive bioadhesive gels composed of cellulose derivatives designed as ophthalmic viscosurgical devices", Biomaterials, 2005, pp. 571-580, vol. 26.
Burhop et al., "Biocompatibility of hemodialysis membranes: Evaluation in an ovine model", J. Lab. Clin. Med., 1993, pp. 276-293, vol. 121.
Cai et al., "Synthesis and study of and controlled release from nanoparticles and their networks based on functionalized hydroxypropylcellulose", Macromolecules, 2003, pp. 6559-6564, vol. 36.
Chen et al., "Bone regeneration on computer-designed nano-fibrous scaffolds", Biomaterials, 2006, pp. 3973-3979, vol. 27.
Dalby et al., "Rapid fibroblast adhesion to 27 nm high polymer demixed nano-topography", Biomaterials, 2004, pp. 77-83, vol. 25.
Dalby et al., "Group analysis of regulation of fibroblast genome on low-adhesion nanostructures", Biomaterials, 2007, pp. 1761-1769, vol. 28.
Desai et al., "In vitro evaluation of pluronic F127-based controlled-release ocular delivery systems for pilocarpines", J. Pharm Sci, 1998, pp. 226-230, vol. 87.

(Continued)

*Primary Examiner* — Patrick Lewis
*Assistant Examiner* — Everett White
(74) *Attorney, Agent, or Firm* — Klarquist Sparkman, LLP

(57) ABSTRACT

Scaffold comprises a polymer defining macropores and comprising hydroxypropylcellulose partially substituted by a substituent comprising a self-crosslinkable group, which is crosslinked through the self-crosslinkable group. The macropores have an average pore size larger than 50 microns and are at least partially interconnected. In one method, bicontinuous emulsion comprising a continuous aqueous phase and a continuous polymer phase is formed. The polymer phase comprises hydroxypropylcellulose partially substituted by a substituent comprising a self-crosslinkable group, and is crosslinked through the self-crosslinkable group to form a polymer defining at least partially interconnected pores. In another method, phase separation is induced in a solution comprising a polymer precursor and water to form a bicontinuous emulsion comprising a continuous polymer phase and a continuous aqueous phase. The polymer precursor comprises a self-crosslinkable group and is crosslinked through the self-crosslinkable group in the emulsion to form a polymer defining at least partially interconnected macropores.

19 Claims, 20 Drawing Sheets

(56) References Cited

OTHER PUBLICATIONS

Drury et al., "Hydrogels for tissue engineering: scaffold design variables and applications", Biomaterials, 2003, pp. 4337-4351, vol. 24.

Fischbach et al., "Engineering tumors with 3D scaffolds", Nature Methods, 2007, pp. 855-859, vol. 4.

Ford et al., "A macroporous hydrogel for the coculture of neural progenitor and endothelial cells to form functional vascular networks in vivo", PNAS, 2006, pp. 2512-2517, vol. 103.

Gao et al., "Self-association of hydroxypropylcellulose in water", Macromolecules, 2001, pp. 2242-2247, vol. 34.

Gehrke, "Synthesis, equilibrium swelling, kinetics, permeability and applications of environmentally responsive gels", Adv. Polym. Sci., 1993, pp. 81-144, vol. 110.

Gerecht et al., "A porous photocurable elastomer for cell encapsulation and culture", Biomaterials, 2007, pp. 4826-4835, vol. 28.

Gerecht et al., The effect of actin disrupting agents on contact guidance of human embryonic stem cells, Biomaterials, 2007, pp. 4068-4077, vol. 28.

Griffith et al., "Capturing complex 3D tissue physiology in vitro", Nature Reviews, 2006, pp. 211-224, vol. 7.

Harsh et al., "Modeling swelling behavior of cellulose ether hydrogels", ACS Symp. Ser., 1993, pp. 105-134, vol. 520.

He et al., "Studies on acrylic acid-grafted polyester fabrics by electron beam preirradiation method. II. novel intelligent immersion-resistant and moisture-permeable fabrics", J. Appl. Polym. Sci., 2003, pp. 3939-3943, vol. 89.

Hirsch et al., "Temperature-dependent property development in hydrogels derived from hydroxypropylcellulose", Polymer, 2002, pp. 123-129, vol. 43.

Hu et al., "Polymer Gel Nanoparticie Networks", Adv. Materials, 2000, pp. 1173-1176, vol. 12.

Kabra et al., "Microporous, responsive hydroxypropyl cellulose gels, 1. Synthesis and microstructure", Macromolecules, 1998, pp. 2166-2173, vol. 31.

Khademhosseini et al., "Microscale technologies for tissue engineering and biology", Proc. Natl. Acad. Sci. USA, 2006, pp. 2480-2487, vol. 103.

Lévesque et al., "Macroporous interconnected dextran scaffolds of controlled porosity for tissue-engineering applications", Biomaterials, 2005, pp. 7436-7446, vol. 26.

Lévesque et al., "Synthesis of cell-adhesive dextran hydrogels and macroporous scaffolds", Biomaterials, 2006, pp. 5277-5285, vol. 27.

Lim et al., "The regulation of integrin-mediated osteoblast focal adhesion and focal adhesion kinase expression by nanoscale topography", Biomaterials, 2007, pp. 1787-1797, vol. 28.

Martson et al., "Is cellulose sponge degradable or stable as implantation material? An in vivo subcutaneous study in the rat", Biomaterials, 1999, pp. 1989-1995, vol. 20.

Miller et al., "Endothelial and vascular smooth muscle cell function on poly(lactic-co-glycolic acid) with nano-structured surface features", Biomaterials, 2004, pp, 53-61, vol. 25.

Miyamoto et al., "Tissue biocompatibility of cellulose and its derivatives", J Bio Mater Res, 1989, pp. 125-133, vol. 23.

Ng et al., "Optimization of 3-D hepatocyte culture by controlling the physical and chemical properties of the extra-cellular matrices", Biomaterials, 2005, pp. 3153-3163, vol. 26.

International Preliminary Report on Patentability, dated Jun. 22, 2010, in related PCT patent application No. PCT/SG2008/000491.

Sannino et al., "Synthesis and characterization of macroporous poly (ethylene glycol)-based hydrogels for tissue engineering application", J. Biomed. Mater. Res., 2006, pp. 229-236, vol. 79A.

Sardonini, "Design and operating criteria for hollow fiber bioreactors", Bioprocess Eng., 1996, pp. 327-330, vol. 15.

Seglen, "Chapter 4: Preparation of isolated rat liver cells", Methods Cell Biol., 1976, p. 29-83, vol. 13.

Sevillano et al., "Cellulose acetate membrane improves some aspects of red blood cell function in haemodialysis patients", Nephrol Dial Transplant, 1990, pp. 497-499, vol. 5.

Tabata et al., "Recent progress in tissue engineering", Drug Discovery Today, 2001, pp. 483-487, vol. 6.

Trojani et al., "Three-dimensional culture and differentiation of human osteogenic cells in an injectable hydroxypropylmethylcellulose hydrogel", Biomaterials, 2005, pp. 5509-5517, vol. 26.

Vlierberghe et al., "Porous gelatine hydrogels: 1. Cryogenic formation and structural analysis", Biomacromolecules, 2007, pp. 331-337, vol. 8.

Webb et al., "Biodegradable polyester elastomers in tissue engineering", Expert Opin. Biol. Ther., 2004, pp. 801-812, vol. 4.

Webb et al., "Biodegrable poly(diol citrate) nanocomposite elastomers for soft tissue engineering", J. Mater. Chem., 2007, pp. 900-906, vol. 17.

Wu et al., "Phase Behavior of thermally responsive microgel colloids", Phys. Rev. Lett., 2003, pp. 048304-1 to 048304-4, vol. 90.

Extended European Search Report, dated Sep. 16, 2013, in related European patent application No. 08863269.0.

\* cited by examiner

FORMING POROUS SCAFFOLD FROM CELLULOSE DERIVATIVES

CROSS REFERENCE TO RELATED APPLICATIONS

This is a division of application Ser. No. 12/824,105, filed Jun. 25, 2010, now U.S. Pat. No. 8,283,028 which is a continuation-in-part of application Ser. No. 12/809,534, filed Jun. 18, 2010, now abandoned which was the National Stage of International Application No. PCT/SG2008/000491, filed Dec. 18, 2008, which claims the benefit of U.S. Provisional Application No. 61/006,090, filed Dec. 18, 2007, the entire contents of each of which are incorporated herein by reference.

FIELD OF THE INVENTION

The present invention relates to porous scaffolds and methods of forming such scaffolds.

BACKGROUND OF THE INVENTION

There are many different techniques for forming macroporous scaffolds, such as salt leaching, gas foaming, emulsion freeze drying, fibrous fabric processing, and 3D (three dimensional) printing. Macroporous scaffolds are useful for supporting cells as the large pores can facilitate migration and growth of the cells inside the pores and allow sufficient nutrient access and removal of metabolites. It has been reported that when hydroxypropylcellulose (HPC) is crosslinked at different temperatures, both non-porous and microporous HPC hydrogels can be formed. The average pore sizes in reported microporous HPC hydrogels are less than 10 microns. Generally, micropores refer to pores that have an average pore size in the range of 2 to 50 microns, and macropores refer to pores that have an average pore size of larger than 50 microns.

SUMMARY OF THE INVENTION

It has been recognized that in some applications it is desirable to form macroporous scaffolds from cellulose derivatives such as HPC derivatives. It has also been surprisingly discovered that macroporous scaffolds can be formed from hydroxypropylcellulose partially substituted by a substituent, where the substituent comprises one or more self-crosslinkable groups. For example, the substituent can be allyl isocyanate. The macroporous scaffold formed from such partially substituted hydroxypropylcellulose can also have a relatively high interconnected porosity, such as about 50% or higher. The partially substituted hydroxypropylcellulose may be replaced by another thermo-sensitive polymer precursor, such as methylcellulose partially substituted by a substituent that comprises a self-linkable group, or a pH-sensitive polymer precursor partially substituted by a substituent that comprises a self-linkable group.

Therefore, in accordance with an aspect of the present invention, there is provided a scaffold comprising a polymer defining macropores and comprising hydroxypropylcellulose partially substituted by a substituent, the substituent comprising a self-crosslinkable group, the partially substituted hydroxypropylcellulose being crosslinked through the self-crosslinkable group, the macropores having an average pore size of larger than 50 microns and being at least partially interconnected. The polymer may have an interconnected porosity of about 50% or higher. The polymer may have a total porosity of about 80% or higher. The macropores may have a pore size distribution peaking at above 50 microns, such as at about 90 or about 100 microns. The polymer may have an equilibrium water content of about 85%. The polymer may have a Young's modulus of about 10 to about 20 kPa in a hydrated state. The self-crosslinkable group may comprise an unsaturated double carbon-carbon bond. The substituent may comprise allyl isocyanate, methacrylic acid, acrylic acid, or glycidyl methacrylate. The partially substituted hydroxypropylcellulose may have a degree of substitution of less than about 2.5, such as about 2.1. The polymer may be a gel, such as when in a hydrated state.

In accordance with another aspect of the present invention, there is provided a method of forming a scaffold, comprising forming a bicontinuous emulsion comprising a continuous aqueous phase and a continuous polymer phase, the polymer phase comprising hydroxypropylcellulose partially substituted by a substituent, the substituent comprising a self-crosslinkable group; crosslinking the partially substituted hydroxypropylcellulose through the self-crosslinkable group to form a polymer defining at least partially interconnected pores. The substituent may comprise allyl isocyanate, methacrylic acid, acrylic acid, or glycidyl methacrylate. The pores may comprise macropores. The crosslinking may comprise irradiating the emulsion with γ-ray. The crosslinking may comprise crosslinking at least about 90 wt % of the partially substituted hydroxypropylcellulose in the emulsion. Water may be removed from the pores by freeze-drying the polymer. After the freeze-drying, the polymer may have an interconnected porosity of about 50% or higher, and the pores may have an average pore size of larger than 50 microns. The emulsion may comprise about 80 to about 90 wt % of the aqueous phase and about 10 to about 20 wt % of the polymer phase. The partially substituted hydroxypropylcellulose may have a degree of substitution of about 2.5 or less, such as about 2.1. The polymer may be a gel, such as when in a hydrated state. The emulsion may be formed by subjecting a solution comprising water and the partially substituted hydroxypropylcellulose to heat treatment. The heat treatment may comprise heat treatment at a temperature of about 313 K for about 5 minutes.

In accordance with a further aspect of the present invention, there is provided a method of forming a scaffold, comprising inducing phase separation in a solution comprising a polymer precursor and water, to form a bicontinuous emulsion comprising a continuous polymer phase and a continuous aqueous phase, the polymer precursor comprising a self-crosslinkable group; crosslinking the polymer precursor through the self-crosslinkable group in the emulsion to form a polymer defining at least partially interconnected macropores. The polymer precursor may be a cellulose derivative. The cellulose derivative may be a methylcellulose derivative, or a hydroxypropylcellulose derivative, such as hydroxypropylcellulose partially substituted by allyl isocyanate. The cellulose derivative may be partially substituted by a substituent that comprises a self-linkable group. The self-crosslinkable group may comprise an unsaturated double carbon-carbon bond. The substituent may comprise allyl isocyanate, methacrylic acid, acrylic acid, or glycidyl methacrylate. The polymer precursor may be thermo-sensitive, and the inducing phase separation may comprise heating the solution. The polymer precursor may be pH-sensitive, and the inducing phase separation may comprise changing pH of the solution. The crosslinking may comprise irradiating the emulsion with γ-ray. The polymer may be a gel, such as when in a hydrated state.

There is also disclosed a scaffold which comprises a crosslinked polymer that defines macropores. The macropores are at least partially interconnected and have an average pore size of larger than 50 microns. The interconnected porosity may be about 50% or higher. The polymer is formed from a polymer precursor that is responsive to a phase separation stimuli to undergo phase separation in an aqueous solution. The stimuli may be heat or pH change in the solution. The polymer precursor also comprises a self-crosslinkable group so that the polymer molecules are crosslinked through the self-crosslinkable group. The crosslinkable group may be selected so that it will crosslink with each other when irradiated with γ-ray. The polymer precursor may be a cellulose derivative. The cellulose derivative may be a methylcellulose derivative, or a hydroxypropylcellulose derivative, such as hydroxypropylcellulose partially substituted by allyl isocyanate. The cellulose derivative may be partially substituted by a substituent that comprises a self-linkable group. The self-crosslinkable group may comprise an unsaturated double carbon-carbon bond. The substituent may comprise allyl isocyanate, methacrylic acid, acrylic acid, or glycidyl methacrylate. The polymer may have a total porosity of about 80% or higher. The macropores may have a pore size distribution peaking at above 50 microns, such as at about 90 or about 100 microns. The polymer may have an equilibrium water content of about 85%. The polymer may have a Young's modulus of about 10 to about 20 kPa in a hydrated state. The polymer may have a degree of substitution of less than about 2.5, such as about 2.1. The polymer may be a gel, such as when in a hydrated state.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
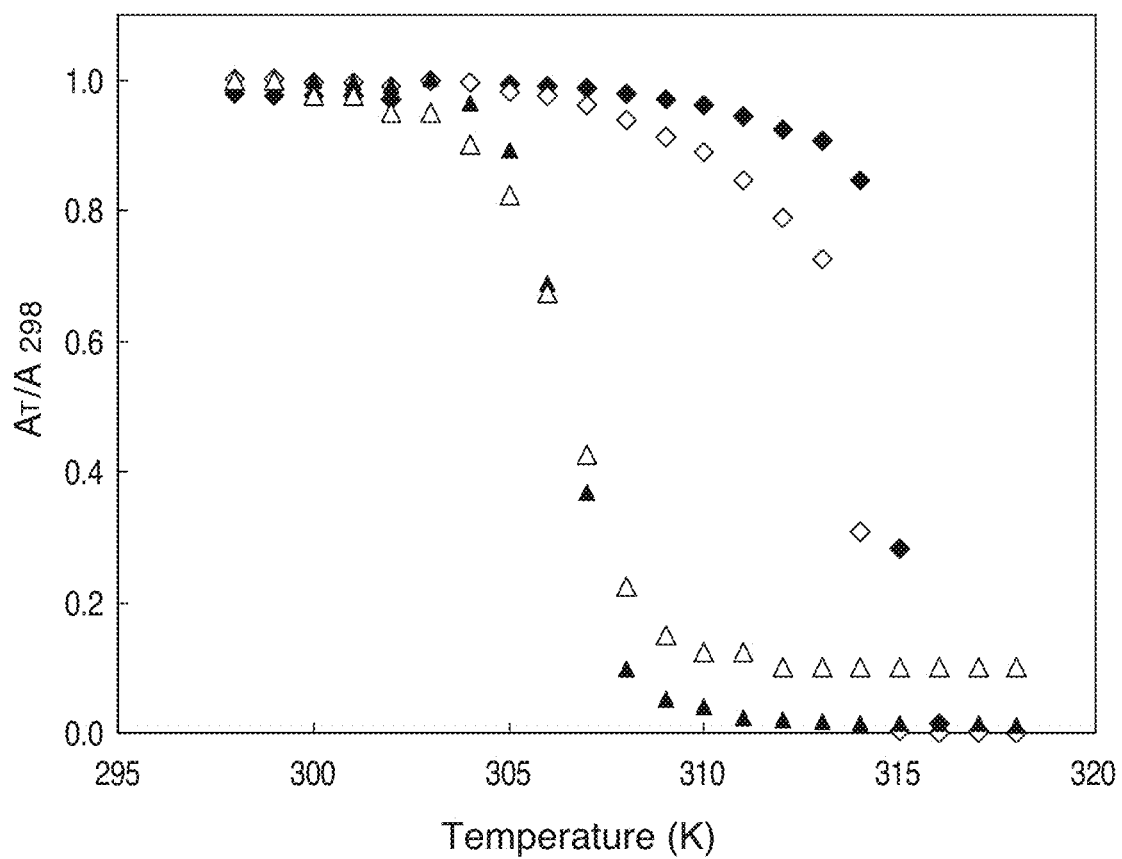
FIG. 1 is a data graph showing the dependence of UV absorbance on solution temperature for different sample solutions.

An exemplary embodiment of the present invention relates to a scaffold that is formed of crosslinked hydroxypropylcellulose partially substituted by allyl isocyanate (H-A). A scaffold is any porous material or structure that can be used to provide a supporting framework to support something else, such as cells or tissues. The pores of the H-A polymerl are macropores of an average pore size of larger than 50 microns. The H-A polymer when hydrated may form a gel.

In one embodiment, the H-A polymer has an interconnected porosity of about 50% or higher, and may have a total porosity of about 80% or higher. The interconnected porosity refers to the extent of connection between adjacent pores, and can be determined by mercury intrusion porosimetry.

The macropores may have a pore size distribution peaking at above 50 microns, such as at about 90 or about 100 microns. The peak may be determined from the pore size distribution curves obtained by mercury intrusion porosimetry.

The pore sizes and their distribution in a scaffold may be determined using a porosimeter, such as a PASCAL 140 mercury porosimeter, available from Thermo Finnigan™.

The pore sizes may be measured when the H-A polymer is in a hydrated state or dehydrated state, depending on the technique used.

The H-A polymer may have an equilibrium water content (EWC) of about 85%, and a Young's modulus of about 10 to about 20 kPa in a hydrated state. The equilibrium water content (EWC) is calculated as $EWC = 100\% \times (W_h - W_d)/W_h$, where $W_d$ is the dry weight of the gel and $W_h$ is the fully hydrated weight of the H-A polymer.

The H-A molecules may have a degree of substitution (DS) of about 2.5 or less, such as about 2.1. The DS may be adjusted by varying the molar ratio of —OH in HPC to —NCO in allyl isocyanate. The DS may be determined using nuclear magnetic resonance (NMR) spectroscopy, as can be understood by persons skilled in the art.

Another exemplary embodiment of the present invention relates a process for preparing a scaffold, such as the scaffold described above. In this process, a bicontinuous emulsion is prepared, which contains a continuous aqueous phase and a continuous polymer phase. The polymer phase contains H-A molecules as a polymer precursor. The DS of H-A may be about 2.5 or less, such as about 2.1. The H-A molecules are crosslinked to form a polymer with at least partially interconnected macropores. The emulsion may be irradiated with γ-ray to induce crosslinking between the H-A molecules. The emulsion may be selected and irradiated such that at least about 90 wt % of the H-A molecules (polymer precursor) are crosslinked (i.e. the degree of crosslink is 90 wt %). The H-A polymer will initially form a gel containing water or an aqueous phase in the macropores after crosslinking, which may be removed such as by freeze-drying the gel. The contents of the emulsion may be adjusted so that, after freeze-drying, the resulting polymer has an interconnected porosity of about 50% or higher, and the macropores have an average pore size of larger than 50 microns. The pore size distribution may peak at above about 50 microns, such as at about 90 or about 100 microns. For example, the emulsion may include about 80 to about 90 wt % of the aqueous phase and about 10 to about 20 wt % of the polymer phase (or H-A)

Several factors may affect the values of total porosity, interconnected porosity, and pore size distribution. These factors include polymer precursor concentration, the DS, crosslinking time, and the concentration of any crosslinker. These factors may be adjusted to control the porosity of the resulting scaffold. For example, increasing polymer precursor concentration or crosslinking time may reduce the pore sizes of the scaffolds.

In one embodiment, the bi-phase emulsion may be formed by subjecting an aqueous solution of H-A to heat treatment at a temperature of about 313 K for about 5 minutes to effect phase separation in the solution.

Conveniently, the scaffolds prepared as described herein can have certain benefits and advantages and can be used in various applications such as various medical or biological applications.

In some conventional techniques, macroporous hydrogels are prepared in complex procedures and their pores are not interconnected. The pores in these conventional hydrogels also lack depth distribution and tend to stay close to the surface. In contrast, embodiments of the present invention can provide 3D scaffolds where the interconnected macropores are distributed substantially uniformly in the entire 3D material. The scaffold disclosed herein can be prepared using relatively simple chemistry in a relatively simple fabrication procedure. In some embodiments, the process can be performed in a simple one step chemistry under mild temperature conditions, without using any organic solvent or additional agent (such as surfactant or crosslinking agent).

As can be appreciated, cellulose (poly(1,4'-anhydro-β-D-glucopyranose)) is a major ECM component of plant cells. It is naturally abundant, biocompatible, biodegradable, biorenewable and easily derivatizable. Cellulose-based materials can therefore be conveniently used in pharmaceutical and biomedical applications. The main raw materials used in embodiments of the present invention, such as HPC, can thus be obtained at a relatively low cost.

Hydroxypropylcellulose (HPC) is a derivative of cellulose and is readily available from commercial sources. It has been approved by the United State Food and Drug Administration (FDA) for use in drug delivery applications. HPC and H-A have high solubility in both water and a wide range of organic solvents. They are relatively easy to functionalize to meet various specific requirements in particular applications. An aqueous solution of HPC or H-A can undergo a unique low critical solution temperature (LCST) phase transition from an isotropic aqueous phase to a metastable bi-phase emulsion. This phase separation allows the formation of macroporous polymers and gels.

While microporous hydrogels and nanostructured hydrogels can be formed using other HPC derivatives, it has been recognized that a macroporous hydrogel would have certain benefits over hydrogels with smaller pores and it has been surprisingly discovered that a bi-phase emulsion containing a H-A phase can be conveniently utilized to form macroporous hydrogels.

HPC may be partially substituted with another suitable substituent, instead of ally isocyanate. For example, methacrylic acid, acrylic acid, glycidyl methacrylate, or the like may be a suitable substituent in some applications.

The inherent thermo-sensitive phase behavior of the H-A polymer precursor makes it convenient to form bicontinuous polymer-rich and water-rich phases in the solution by subjecting the solution to heat treatment. Conveniently, it is not necessary to add any chemical solvent or agent (e.g. surfactant) to form the bicontinuous emulsion.

The liquid biphasic structure can be stabilized (solidified) by crosslinking, which in turn may be efficiently effected with γ-ray irradiation. While crosslinking of H-A may be effected using other techniques, γ-Ray irradiation may be advantageous in some applications. For instance, γ-ray can penetrate deeper into a target material than some other types of curing light. Thus, crosslinking in the solution can be activated uniformly at different depths with γ-ray. γ-ray irradiation does not give rise to many undesired side chemical effects and do not require any chemical initiator. Thus, it is a chemically "clean" technique.

It has been found that H-A with a degree of substitution of about 2.5 or less, such as about 2.1, may be advantageous in some applications. For example, H-A polymer precursors with a higher DS tend to have a lower solubility in water but crosslinked H-A polymer with a lower DS may have inferior mechanical properties as compared to H-A polymer with a higher DS. Thus, a balance between different desirable properties may be achieved with a DS of about 2.1 in some applications.

The mechanical properties such as mechanical strength of the H-A scaffolds may be controlled by varying the degree of crosslinking therein. The degree of crosslinking may be controlled by varying H-A concentration in the precursor solution and the crosslinking time. The ability to control mechanical properties of the H-A scaffolds can be advantageous in some applications. For example, it may be desirable to be able to adjust the mechanical properties to provide suitable mechanical stability and structural integrity for supporting cells.

Therefore, the H-A polymer described herein can form three-dimensional (3D) scaffolds for use as soft tissues. The scaffolds can be made to have various desirable physiochemical, mechanical and bio-interfacial properties. For example, the scaffold may have properties that are suitable for promoting cell adhesion. The scaffolds can be made relatively soft and are inherently hydrophilic. The interconnected macropores can facilitate cell growth into the scaffold with cell densities similar to biological tissues. Due to the 3D interconnected macropores, the scaffolds not only can have relatively high equilibrium water content (EWC), be biocompatible, and sustain gradual release of bioactive molecules, but can also support cell growth, migration, and ultimately, tissue formation. The scaffolds also allow ready incorporation of extracellular matrix (ECM) cues to regulate cell and tissue functions. In embodiments of the present invention, the choices of material and the fabrication procedure can be flexible so that it is possible to introduce 3D ECM cues for regulation of cellular functions.

As a water soluble precursor can be used for preparing the scaffold, it may be possible to adjust the degradation profile of the scaffold by modifying the side chain chemistry of the polymer.

Embodiments of the present invention can also provide 3D scaffolds that have integrated interconnected macroporosity, nanofeatures (surface structures having a nanometer scale dimension, see Examples below), high water content and mechanical integrity suitable for soft tissue engineering. Such scaffolds can exhibit controllable, moderate elasticity, and hydrophilicity, which can be advantageous in providing mechanical stability and structural integrity to cells and tissues. The scaffolds can also have nano-features in the pores, which may play a role in the regulation of cell behavior. The nanofeatures may also be useful for loading of bioactive molecules such as adhesion proteins and growth factors etc to control cell behavior and functions.

With interconnected macroporosity and high equilibrium water content, biocompatibility and mechanical integrity, 3D H-A scaffolds as described herein may be suitable for a wide range of applications in soft tissue engineering and regenerative medicine.

Some embodiments of the present invention may also be suitable for application in in vitro substrates for cell culture and studies of cellular behavior in a 3D environment. 3D cell culture environments more closely mimic in vivo microenvironments than 2D culture environments. 3D scaffolds can therefore serve as ECM analogues to provide biomimicry 3D substrates for cell attachment, growth, migration, function and differentiation, or the like.

Some embodiments of the present invention may also be suitable for use in in vitro 3D tissue models that are based upon human cells for pathological study and drug testing.

Some embodiments of the present invention can be used for in vitro cultivation of cells for the creation of external support organs. The highly interconnected macroporous architecture can provide temporary support to the cultivation of a sufficient cell mass with adequate cell-cell contact. Preliminary results have shown that the primary rat hepatocytes cultured in the scaffolds described herein can maintain their liver-specific functions over a period of one week (see Examples below). Other types of cells can also be cultivated in these scaffolds. Examples for relevant applications include inartificial liver assisted devices (BLAD) to provide essential liver functions for the patients with acute liver failure.

A soft, hydrophilic, and macroporous scaffold may be suitable for cell transplantation in soft tissue and organ repair or regeneration applications.

Some embodiments of the present invention can be used for high content screening for drug discovery and screening. A cellulosic scaffold can be easily fabricated into microplate configuration to provide uniform 3D microenvironments for various cellular assays.

Some embodiments of the present invention can be used for localized and sustained delivery of biologically or pharmaceutically active compounds. When the scaffolds are hydrophilic and have a high water retention ability, they can be conveniently used to incorporate and provide sustained release of bioactive molecules or other substances.

As now can be appreciated, in a different embodiment, HPC may be replaced with another thermo-sensitive polymer precursor that can form a stable bicontinuous emulsion in an aqueous solution in response to heat. For example, methylcellulose may be used to replace HPC. Further, a polymer precursor that can form a stable bicontinuous emulsion in an aqueous solution in response to another type of stimuli, such as a change in pH, may also be used to replace HPC. Thus, a suitable pH-sensitive polymer precursor may be used.

As can also be appreciated, in a different embodiment, allyl isocyanate may be replaced with another suitable substituent that includes a self-crosslinkable group. Self-crosslinkable groups refer to functional groups that can be crosslinked between themselves. For example, a suitable substituent or the crosslinkable group may have an unsaturated C=C bond for providing a crosslinkable site. A suitable substituent should also have a functional group for bonding to HPC, so that the HPC can be partially substituted by the substituent. Suitable replacement for allyl isocyanate may include methacrylic acid, acrylic acid, glycidyl methacrylate, or the like. The substituent may include a multi-functional monomer.

Depending on the particular substituent used, the degree of substitution (DS) should be adjusted to retain sufficient thermo-sensitivity in the substituted HPC to allow convenient phase separation, and to allow sufficient crosslinking of the modified HPC during phase separation.

In view of the disclosure herein, it is possible to provide a scaffold which comprises a crosslinked polymer that defines macropores. The macropores are at least partially interconnected and have an average pore size of larger than 50 microns. The interconnected porosity may be about 50% or higher. The polymer is formed from a polymer precursor that is responsive to a phase separation stimuli to undergo phase separation in an aqueous solution. The stimuli may be heat or pH change in the solution. The polymer precursor also comprises a self-crosslinkable group so that the polymer are crosslinked through the self-crosslinkable group. The crosslinkable group may be selected so that it will crosslink with each other when irradiated with γ-ray. The polymer precursor may be a cellulose derivative. The cellulose derivative may be a methylcellulose derivative, or a hydroxypropylcellulose derivative, such as hydroxypropylcellulose partially substituted by allyl isocyanate. The cellulose derivative may be partially substituted by a substituent that comprises a self-linkable group. The self-crosslinkable group may comprise an unsaturated double carbon-carbon bond. The substituent may comprise allyl isocyanate, methacrylic acid, acrylic acid, or glycidyl methacrylate. The polymer may have a total porosity of about 80% or higher. The macropores may have a pore size distribution peaking at above 50 microns, such as at about 90 or about 100 microns. The polymer may have an equilibrium water content of about 85%. The polymer may have a Young's modulus of about 10 to about 20 kPa in a hydrated state. The polymer may have a degree of substitution of less than about 2.5, such as about 2.1. The polymer may be a gel, such as when in a hydrated state.

In some exemplary embodiments, the polymer of the scaffold may include one or more side chains which include, or are attached to, one or more different functional groups. For example, in one embodiment, the polymer may include hydroxypropylcellulose allyl galactose, where galactose ligands may be present in the side chains. A suitable galactose is β-galactose. Conveniently, a scaffold formed of hydroxypropylcellulose allyl galactose can promote formation of cell spheroids when the scaffold is seeded with certain cells, such as primary rat hepatocyte cells, as primary rat hepatocyte is one of the cell types that are responsive to galactose.

Three dimensional (3D) spheroidal formation may be advantageous in some applications. For example, in liver lobes, there are many stacked layers and some cells will be in the form of spheroids (in vivo) at some point in time. With spheroids, hepatocyte can have more cell-to-cell contact, which may be useful for polarity maintenance and formation of bile canaliculi junction (as excretory function). It has been shown that the hepatocytes in spheroids form will have cortical actin (less stress fibers formed), similar to actin in liver lobe.

Galactose can also be a useful ligand for interaction with hepatocyte cell membrane (asialo glyco receptor), which can be utilized to improve the maintenance of hepatocyte differentiated functions.

Conjugating galactose, such as β-galactose, to the scaffold polymer may be useful for in vitro hepatotoxicity drug testing. To this end, the pore sizes in the scaffold may be selected to be below about 200 microns, such as from about 100 to about 150 microns.

A scaffold according to an exemplary embodiment of the present invention can be used for testing hydrophobic drugs. In this case, the scaffold material may include electrically charged molecules or groups conjugated to the side chains of the scaffold, to reduce adsorption of hydrophobic substances onto the scaffold. When the surface material of a scaffold used to culture the cells is electrically neutral, a significant amount of hydrophobic drug (or protein) can be absorbed on the scaffold surface. Thus, to reduce surface absorption, a biocompatible cationic polymeric group may be conjugated to the side chains of partially substituted hydroxypropylcellulose. The presence of such charged groups can increase the polarity at the surface, which tends to repel more hydrophobic substances, and thus reduce hydrophobic drug absorption on the surface. The charged groups may be conjugated onto the side chains before the scaffold is formed or shaped. Potentially useful charged groups include polylysine, polyethylene imine, and polypropyleneimine hexadecaamine. Other charged groups or polymers that are known to be biocompatible with cell culture or gene delivery vector may also be used as the charged groups, depending on the application.

A biocompatible cationic polymeric group may be attached, such as conjugated to a side chain of the scaffold polymer. Exemplary biocompatible cationic polymeric groups include polylysine, polyethylene imine, or polypropyleneimine hexadecaamine. A biocompatible group is non-toxic to the cells that may come into contact with the scaffold. For example, the biocompatible cationic polymeric group may be attached to a galactose ligand in hydroxypropylcellulose allyl galactose.

The side chains of a scaffold polymer may also include other functional groups, examples of which include cell attachment ligands such as arginine-glycine-aspartic acid (RGD); ECM for livers such as collagen, laminin, or fibronectin; and cell growth factors such as hepatocyte growth factors (HGF) conjugated with a spacer. These functional groups may be attached or conjugated to the side chains of the polymer or the partially substituted hydroxypropylcellulose. One or more of these groups may also be attached to a surface of the scaffold after its formation. ECM materials such as collagen Type I, or growth factors, may be attached to the scaffold surface to adjust, or promote, cell differentiation.

While some variation and modification of the exemplary embodiments and their applications are discussed herein, they are for illustration purposes and are not exhaustive. Other applications of the embodiments of the present invention are also possible.

EXAMPLES

All raw chemical materials used in these examples were obtained from Sigma-Aldrich Pte Ltd.™, Singapore, unless otherwise specified.

Example I

Synthesis of Allyl Carbamate of HPC (H-A)

HPC ($M_n \approx 10,000$; degree of etherification was about 3.4, as determined by $^1$H NMR) was dehydrated by azeotropic distillation in toluene.

The dehydrated HPC (2.0 g, 6.0 mmol [OH]) was dissolved in chloroform (100 ml), to which a solution of allyl isocyanate (1.83 ml, 3.5 molar equivalents) in chloroform (10 ml) was added dropwise. After one drop of dibutyltin dilaurate was added as a catalyst, the reaction mixture was stirred at room temperature for about 48 hours, then concentrated using a rotatory evaporator and precipitated into diethyl ether.

The reaction product was collected by vacuum filtration, and purified by re-dissolution in chloroform and precipitation into diethyl ether. The residual impurities were removed by Soxhlet extraction from diethyl ether.

The product contained, according to $^1$H NMR analysis (CDCl$_3$, δ ppm): 0.5-1.5 (—CH$_3$), 5.7-6.1 (—CH=CH$_2$), 2.5-5.3 (all other protons).

The degree of substitution was 2.1, as calculated by $^1$H NMR recorded in CDCl$_3$.

The temperature-mediated phase behavior of the sample H-A solutions at 10 wt % and 20 wt % (weight percentage of H-A in the solution) was investigated on a UV/VIS/NIR spectrophotometer (Jasco™, V-570, Japan), by measuring the optical densities at 480 nm as a function of temperature. The temperatures of sample holders were controlled using a Jasco PSC-498 temperature controller. The samples were allowed to reach equilibrium at each temperature for 10 min before the readings were taken. Representative measurement results are shown in FIG. 1. The occurrence of phase separation was indicated by reduction in optical density. The temperature at which the reduced optical density reached a plateau was selected as the operating temperature for inducing phase separation of H-A solutions and subsequent crosslinking.

FIG. 1 shows representative measured data indicating the temperature-dependences of normalized (normalized to the absorption intensity at 298 K) UV absorption of sample solutions containing different concentrations of HPC (diamonds: 10 wt %—solid, 20 wt %—hollow) and H-A (triangles: 10 wt %—solid, 20 wt %—hollow). The phase transition is manifested by a precipitous decrease in the transmittance upon increasing temperature. The temperature at which the sample transmittance decreased by 50% is denoted herein as LCST. Compared to HPC, the phase separation in H-A solutions of both 10 wt % and 20 wt % took place at a lower temperature range, with LCST being about 307 K, resulting from hydrophobic substitution with allyl groups.

Like the HPC samples, the H-A samples became white and opaque when the temperature was increased, but without any noticeable sedimentation over the temperature range studied, indicating the formation of stable colloidal systems in the H-A solutions.

Stable colloidal formation can be advantageous for subsequent generation of 3D open porous structures.

Based on the experimental data, 313 K was selected as a suitable temperature for induction of phase separation and crosslinking of H-A solutions.

Example II

Preparation of 3D H-A Scaffolds

Sample solutions of H-A and water were prepared. The solutions contained about 10 or about 20 wt % of H-A respectively. The water was degassed and deionised before mixed with H-A.

In a representative procedure, a glass vials (10 mm in diameter×50 mm height) containing a sample H-A solution was placed in a water bath at 313 K for 5 min to induce phase separation in the solution to form a bicontinuous emulsion.

The emulsion was transferred, in a beaker containing water at 313 K, to a gamma irradiator (Gammacell 220, MDS Nordion™, Canada), and subjected to γ-ray irradiation at a dose rate of 10 kGy h$^{-1}$ for 30 min, to crosslink the polymeric phase in the emulsion to form a gel.

The crosslinked gel was freeze-dried, washed with deionised water for one week with daily water change, and lyophilized for storage.

The sample polymer (scaffold) formed with 10 wt % H-A is referred to as Sample I, and the sample polymer (scaffold) formed with 20 wt % H-A is referred to as Sample II.

Example III

Comparison Samples

For comparison purposes, H-A solutions as prepared in Example II were also crosslinked at temperatures from about 273 to about 277 K, without phase separation, by irradiation as described in Example II. The resulting products were homogenous gels and were subjected to similar post-irradiation treatment as described in Example II.

These gels were referred to as Sample IC (for 10 wt % H-A) and Sample IIC (for 20 wt % H-A).

Example IV

Characterization of Sample Scaffolds

The degree of crosslink in the samples was expressed as the weight percentage of the crosslinked fraction of the scaffold.

Residual soluble polymers were removed by Soxhlet extraction with acetone for 4 h.

The lyophilized scaffolds were allowed to swell in water at room temperature for 48 h. The samples were weighed before and after this hydration process. The EWC of the sample scaffolds were determined based on their dry and hydrated weights, according to the equation discussed above.

The Mechanical properties of hydrated scaffolds were evaluated by compression tests on an Instron™ Micro-Tester 5848 (Instron Co., Canton, Mass., U.S.A.), at a speed of 0.5 mm/min and a temperature of 25±2° C. The compression moduli were calculated from the slopes of the initial linear portion of the stress-strain curves.

The pore size distribution in the sample scaffolds was determined using a PASCAL 140 mercury porosimeter (Thermo Finnigan. Italy, S.p.A.) with S-CD6 dilatometer.

Cross-sectional surfaces of sample lyophilized H-A scaffolds were sputter coated with gold and examined on a field-emission scanning electron microscope (FESEM) (JEOL™, JSM-7400M, Japan) at an accelerating voltage of 20 kV. The morphology of the hydrated H-A scaffolds was investigated by laser confocal fluorescence microscopy. The freeze-dried scaffolds were stained overnight with fluorescein isothiocyanate conjugated dextran (FITC-dextran) (1.0 mg ml$^{-1}$) or propdium iodide (PI) (50 μg ml$^{-1}$) in the phosphate-buffered saline (PBS), respectively. They were then washed with PBS for 5 times and examined using a laser confocal fluorescence microscope (Olympus™ Fluoview 300, Japan). Optical sectioning with a Z resolution of 2 μM was used to obtain a 3D image stack of scaffolds.

Some representative results of the above tests are summarized in Table I and shown in the figures.

TABLE I

Properties of Sample H-A Scaffolds

| | Sample I | Sample II |
|---|---|---|
| Porosity (%) | 83 | 92 |
| Interconnected porosity (%) | 52 | 56 |
| Peak pore size (micron) | 103 | 88 |
| EWC (wt %) | 91 | 89 |
| Young's modulus in hydrated state (kPa) | 9.5 | 20.5 |
| Degree of crosslink (wt %) | 90 | 92 |

In Table I, peak pore size refers to the location of the highest peak in the pore distribution, and is the pore size that occurs most frequently in a porous material.

There was no significant observed change in sample dimension due to dehydration or re-hydration. This stability is expected to be due to the extensive (about 90 wt %) crosslinking in the H-A polymer.

Figure 2:
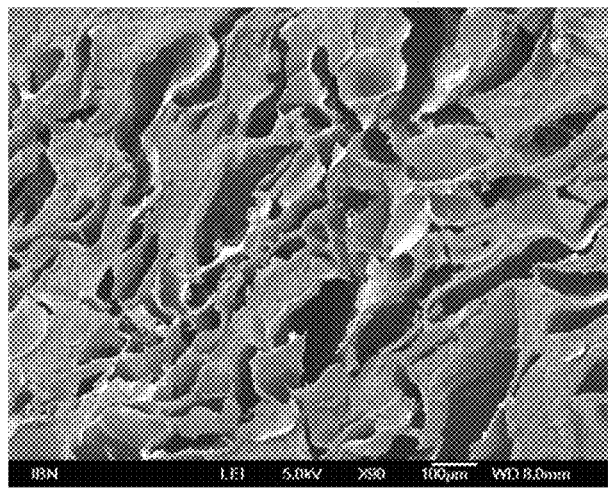
FIG. 2 is a scanning electron microscopy (SEM) image of a cross-section of a sample scaffold.
Figure 3:
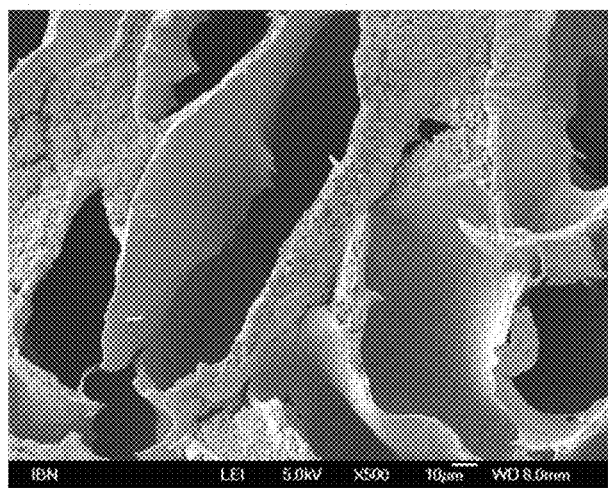
FIGS. 3 and 4 are SEM images of portions of the sample scaffold shown in FIG. 2, with increased magnification.
Figure 4:
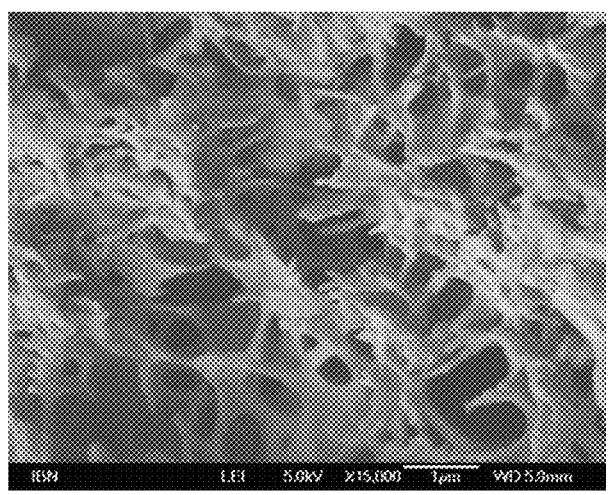

The presence of interconnected macroporous structures in Samples I and II was observed by mercury intrusion porosimetry and scanning electron microscopy (SEM). FIG. 2 is a representative SEM image of Sample II at a magnification factor of 90. Further magnified SEM images of a portion of the image of FIG. 2 are shown in FIGS. 3 (500 magnification) and 4 (15000 magnification). Similar interior morphology of interconnected macroporosity were also observed in Sample I. Nano-scale features and structures on the pore surfaces, such as edges, spikes in the regions connecting the macropores, were also visible in the images.

In contrast to some conventional techniques in which only micropores were formed in HPC scaffolds, the sample scaffolds formed of hydrophobically modified H-A had interconnected macropores. The H-A samples also retained the phase behavior characteristics of HPC, as indicated by the formation of stable, opaque colloidal system over the temperature range studied.

Figure 5:
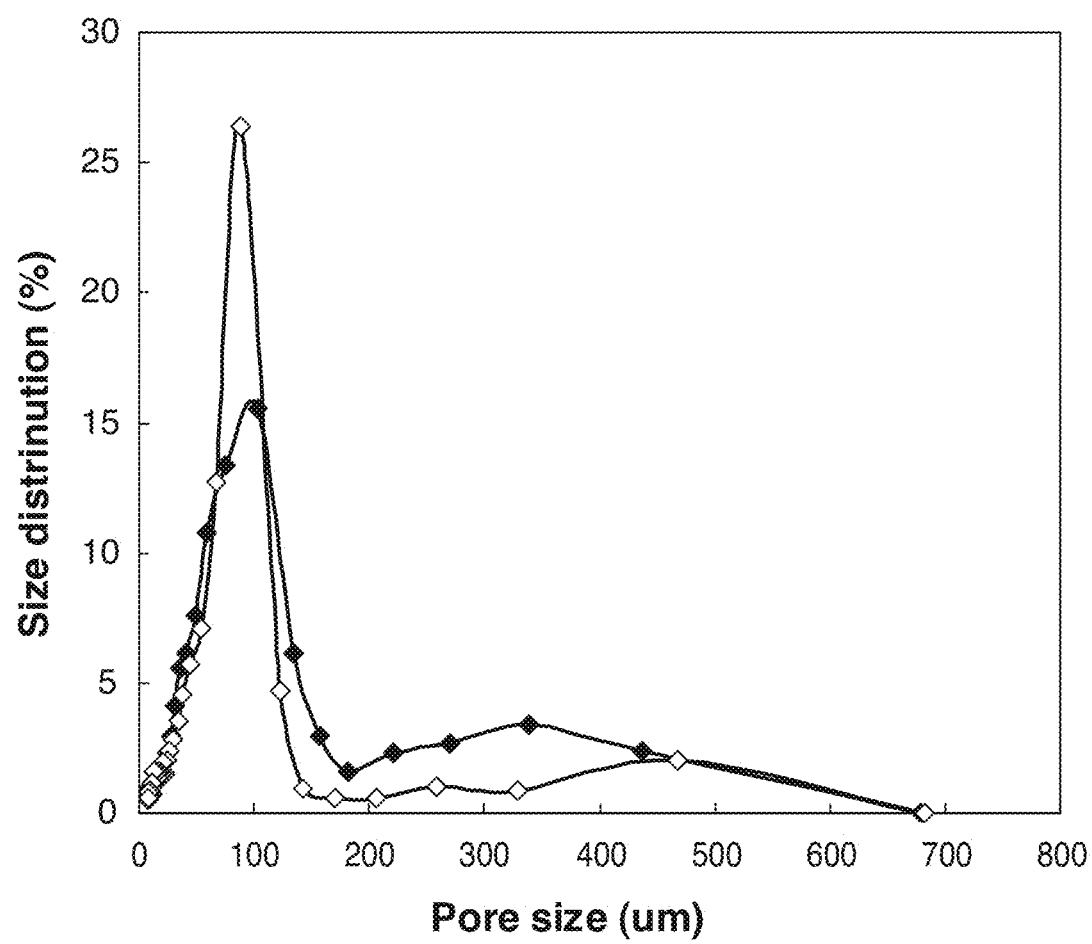
FIG. 5 is a line graph showing the pore size distribution in two sample scaffolds.

Both samples had a broad and bimodal distribution of pore sizes, as shown in FIG. 5 (Sample I—solid; Sample II—hollow), with 50% to 60% interconnected porosity respectively. As can be seen, for both samples, the pore size distribution had two peaks, a taller and sharper peak at a smaller pore size and a shorter and broader peak at a larger pore size. When the H-A concentration was increased, from about 10 wt % to about 20 wt %, the taller peak in the pore size distribution curve was shifted to the left (smaller pore size) and the higher peak was shifted to the right (larger pore size); and the taller peak became taller and the shorter peak became shorter.

The porous structures of Samples II and IIC were also characterized and compared in their hydrated state.

Figure 6:
FIG. 6 is a confocal micrograph of a cross-section of a sample scaffold.
Figure 7:
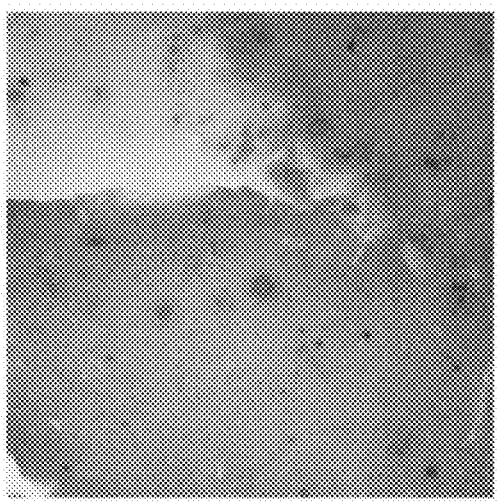
FIG. 7 is a confocal micrograph of a cross-section of a comparison scaffold.

Both Samples II and IIC were stained with FITC-dextran in PBS for 24 hours. A highly porous network was observed in hydrated Sample I in laser confocal microscopy images of the sample. See a representative image in FIG. 6. In comparison, FIG. 7 shows a similar image for Sample IIC, which revealed a nonporous, homogenous structure. This result indicates that phase separation facilitated the formation of interconnected macropores.

Figure 8:
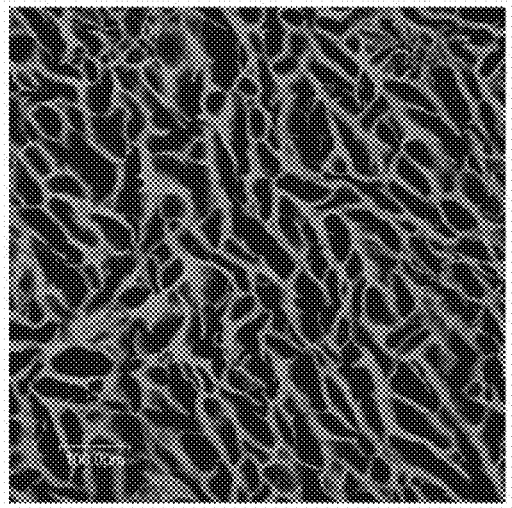
FIG. 8 is a confocal micrograph of the sample scaffold of FIG. 6 but stained with a different marker.
Figure 9:
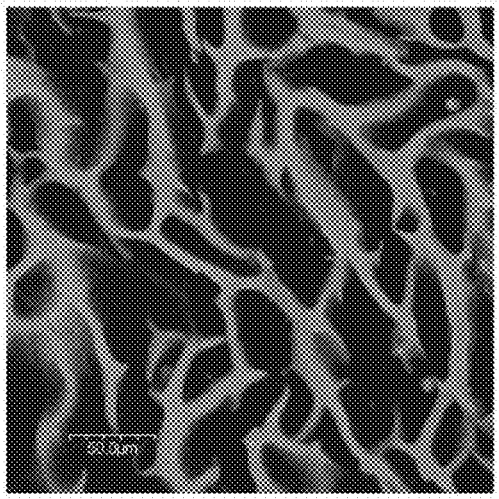
FIG. 9 is a confocal micrograph of the sample scaffold of FIG. 8 but with higher magnification.

The highly macroporous architecture in hydrated Sample II was also confirmed in another staining study using propidium iodide (PI). Representative images of PI-stained Sample II are shown in FIGS. 8 and 9. The sizes of water-filled pores varied broadly from tens to hundreds microns and the thickness of water-swollen struts ranged from about 5 to about 20 microns.

Example V

Cell Culture and Seeding in Sample Scaffolds

For cell culture, Samples I and II were cut into discs of about 10 mm in diameter and about 2 mm in thickness.

NIH 3T3, HepG-2 and MCF-7 cells (ATCC, USA) were cultured according to the standard procedure in high glucose Dulbecco's modified Eagle's medium (DMEM) (Invitrogen™, Singapore) supplemented with 10% fetal bovine serum, 100 unit/ml penicillin and 100 µg/ml streptomycin in a humid incubator at 37° C. and 5% $CO_2$, respectively.

Hepatocytes were harvested from male Wistar rats weighing 250-300 g by a two-step in situ collagenase perfusion method, as described in P. O, Seglen, *Methds Cell Biol.*, 1976, vol. 13, p. 29. Viability of the hepatocytes was ≥90%, as determined by Trypan Blue Exclusion assay. Hepatocytes cultured in the scaffolds were maintained in William's E supplemented with 1 mg/ml bovine serum albumin (BSA), 10 ng/ml epidermal growth factor (EGF), 0.5 µg/ml insulin, 5 nM dexamethasone, 50 ng/ml linoleic acid, 100 unit/ml penicillin and 100 µg/ml streptomycin.

The sample scaffold discs were sterilized in a 12 well plate by gamma irradiation at a dose rate of 10 kGy/h for 4 h. Cell seeding was conducted at a density of $0.5~1.0\times10^6$ cells per scaffold, by adding 20 µl of concentrated cell suspension into each scaffold followed by 200 µl of cell medium. Cell-free scaffold was used as control for all the following work. The scaffolds were incubated for 3 h, after which time 1 ml of cell medium was added, respectively. The viability of cells cultivated in the scaffolds was assessed by fluorescence live/dead staining. The scaffolds were incubated for 30 min with 5 µM Calcein AM (Molecular probe, USA) and 25 µg/ml of propdium iodide in Dulbecco's modified essential medium (DMEM) at 37° C., 5% $CO_2$. Images of live (green) and dead (red) cells were then acquired by laser confocal fluorescence microscopy. Optical sectioning with a Z-resolution of 2 µm was used to obtain a 3D image stack of scaffolds.

Proliferation of NIH 3T3 seeded in sample scaffolds were assessed by monitoring their metabolic activities using almarBlue™ assay. The cell-seeded and cell-free scaffolds were incubated for 4 hours with 10% (v/v) almarBlue (Biosource) in phenol-red free, supplemented DMEM medium. 200 µl of the media from each sample was transferred to a 96-well plate, and the absorbance at 570 nm and 600 nm were measured using a Sunrise™ microplate reader (Tecan, Switzerland). The reduction of almarBlue of each sample was calculated, and converted to cell numbers based upon a standard curve constructed from 2D cell culture with known cell numbers.

Figure 10:
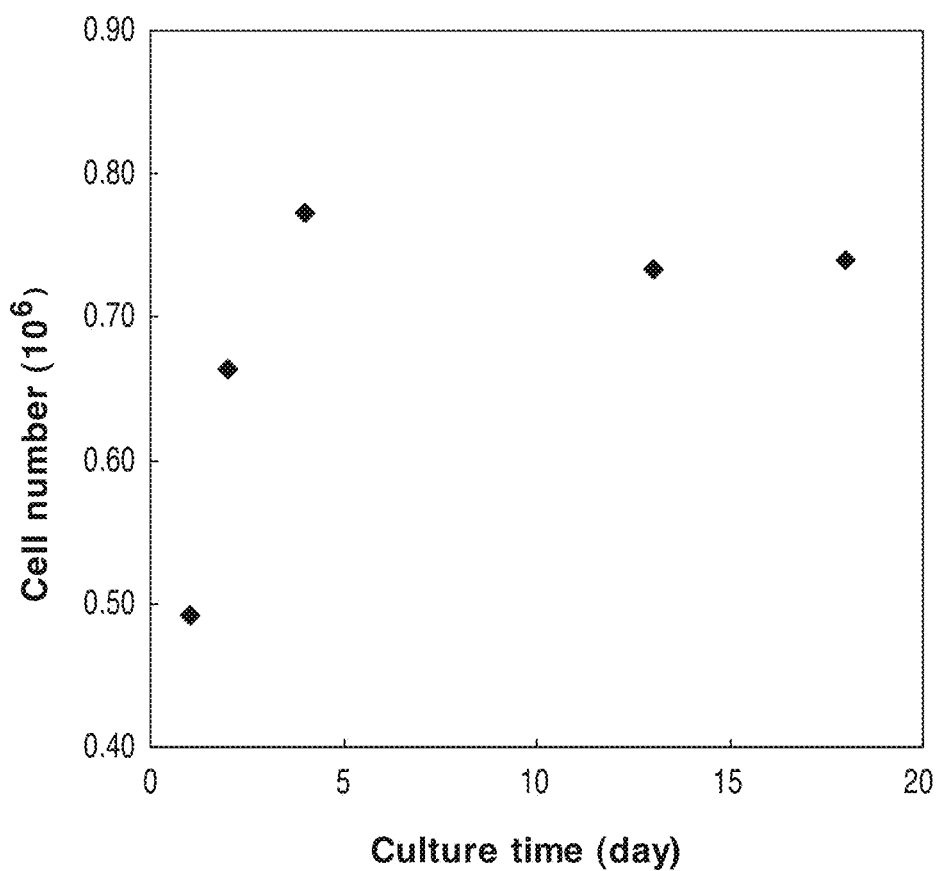
FIG. 10 is a data graph showing the dependence of cell numbers in a sample scaffold on culture time.

Sample II was selected for cellular compatibility tests. A detailed cell viability and proliferation test was conducted on the mouse fibroblast NIH 3T3 cultivated in the scaffold, by measuring the metabolic activity using Alamar Blue assay. The cells were found to be not only viable but also to proliferate well over prolonged culture. The number of cells over time in Sample II was plotted in the graph of FIG. 10.

Figure 11:
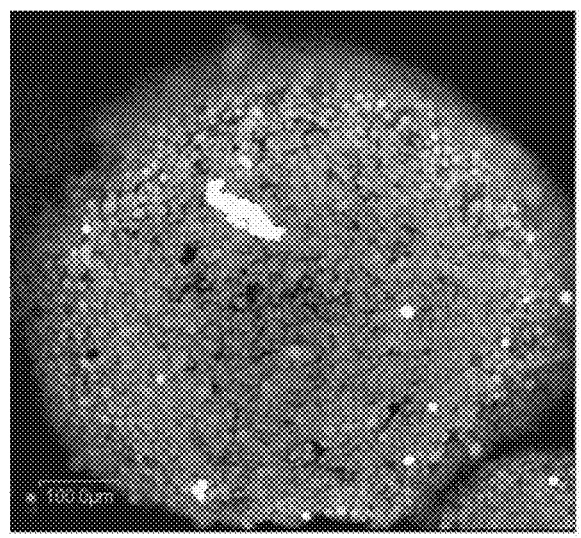
FIGS. 11 and 12 are confocal micrographs of cells cultured in a sample scaffold stained with different markers.
Figure 12:
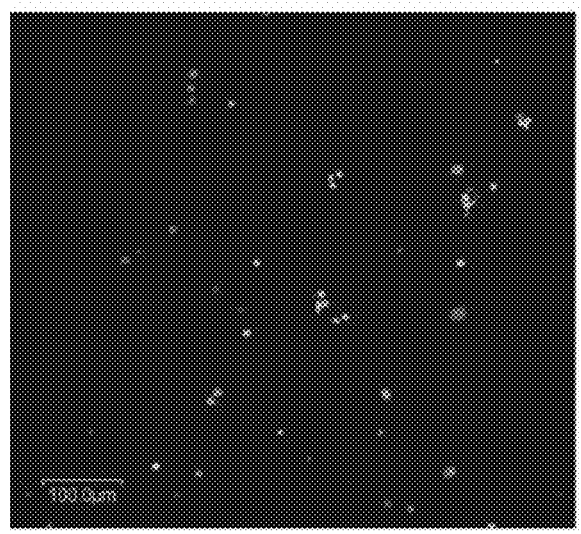
Figure 13:
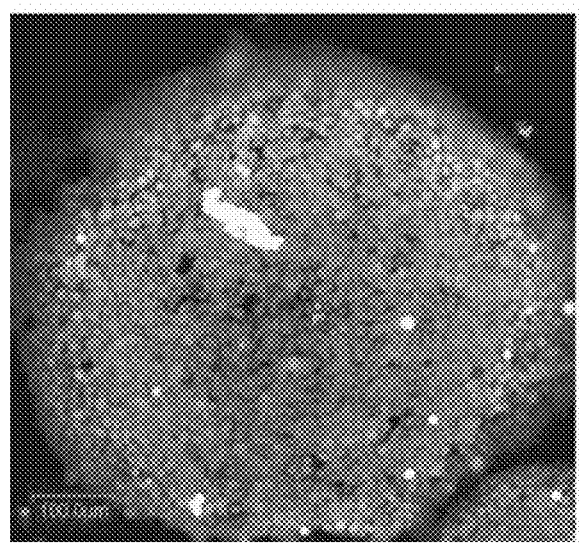
FIG. 13 is a superposition of FIGS. 11 and 12.

FIG. 11 is a fluorescence microscopy image of NIH 3T3 cells cultured in Sample II after 4 weeks of cultivation. The cells were stained with Calcein AM (shown as bright regions in FIG. 11) for live cells. FIG. 12 is a similar image but for cells stained with PI (shown as lighter spots in FIG. 12) for dead cells. FIG. 13 is a superposition of the images of FIGS. 11 and 12.

Figure 14:
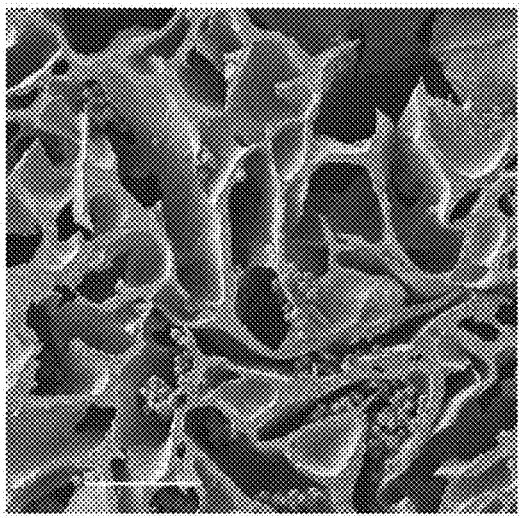
FIGS. 14, 15, 16 and 17 are SEM images of cells cultured in a sample scaffold taken at different times with different magnification, respectively.
Figure 15:
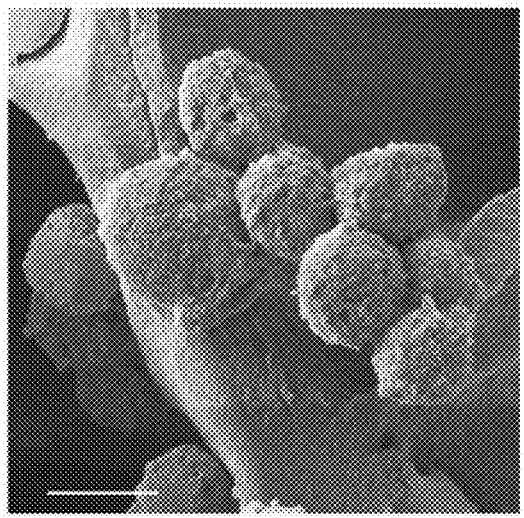
Figure 16:
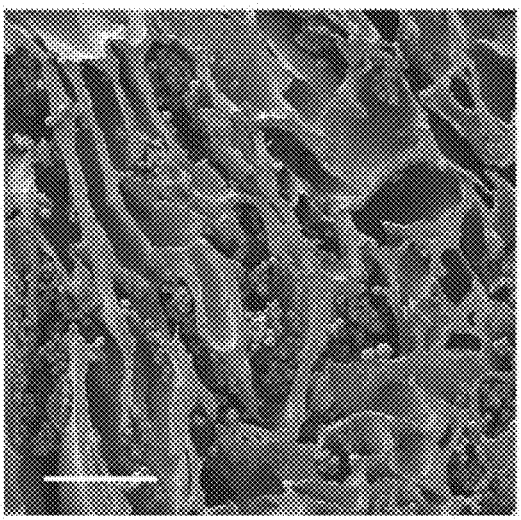
Figure 17:
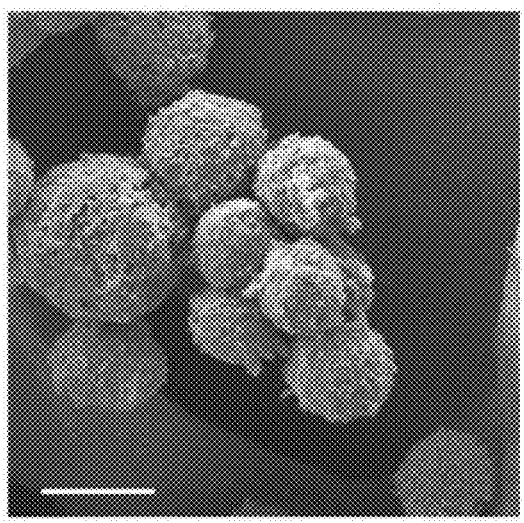

FIGS. 14 and 15 show SEM images of NIH 3T3 cultured in Sample II for one day at different magnifications. FIGS. 16 and 17 show SEM images of NIH 3T3 cultured in Sample II for five days at different magnifications. The scale bars represent 100 microns in FIGS. 14 and 16, and 10 microns in FIGS. 15 and 17.

To investigate the urea synthesis of hepatocytes, the cells cultured in the sample scaffolds were incubated in a culture medium containing 1.0 mM $NH_4Cl$ for 90 min; the medium was analyzed by the Urea Nitrogen Kit (Sigma Diagnostics), as described in S. Ng et al., *Biomaterials*, 2005, vol. 26, p. 3163. The data was normalized by the number of cells seeded in the scaffolds that was quantified using Quan-iT™ PicoGreen dsDNA Assay Kit (Invitrogen, Singapore).

Figure 18:
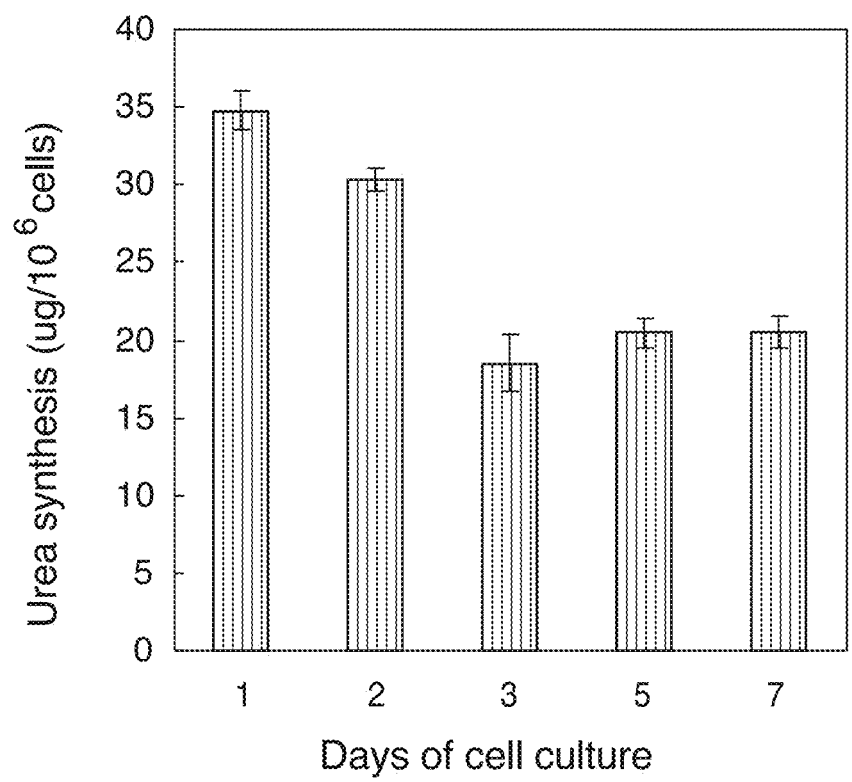
FIG. 18 is a bar graph showing measured urea synthesis data.

Primary hepatocyte has been a major cell source for liver tissue engineering; it tends to lose its hepatic function rapidly in vitro. The present data showed that primary rat hepatocytes cultured in the sample scaffolds could maintain their urea secretion, a liver-specific function, over a period of one week. FIG. 18 shows the measured result.

Figure 19:
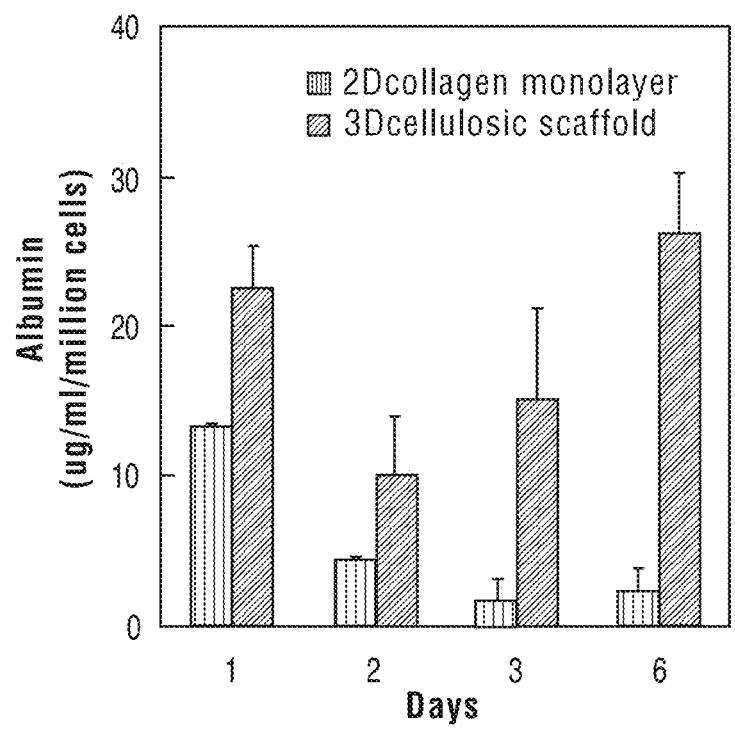
FIGS. 19 and 20 are bar graphs showing measured comparison data.
Figure 20:
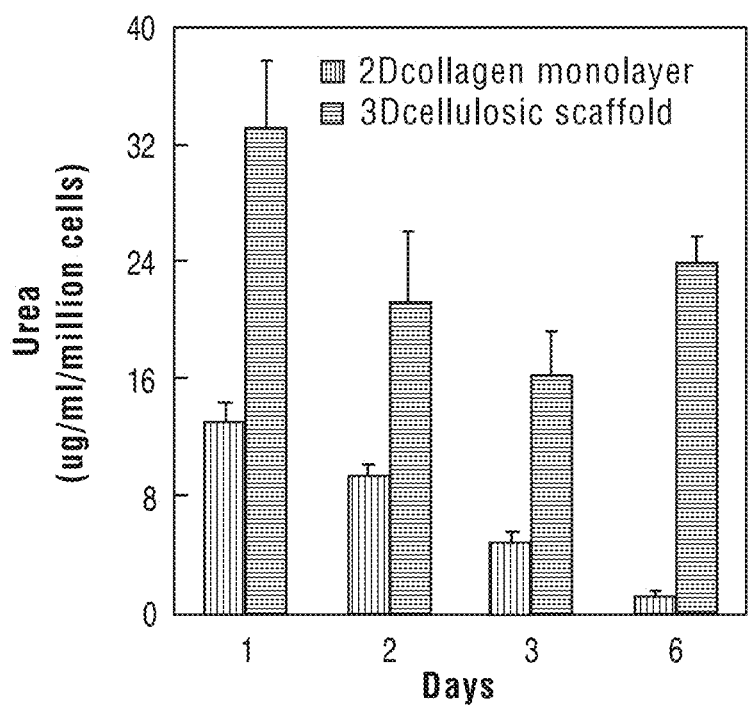
Figure 21:
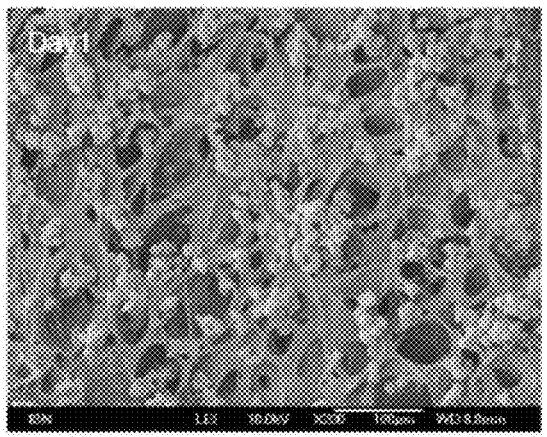
FIGS. 21, 22, 23 and 24 are SEM images of cells cultured in a sample scaffold.
Figure 22:
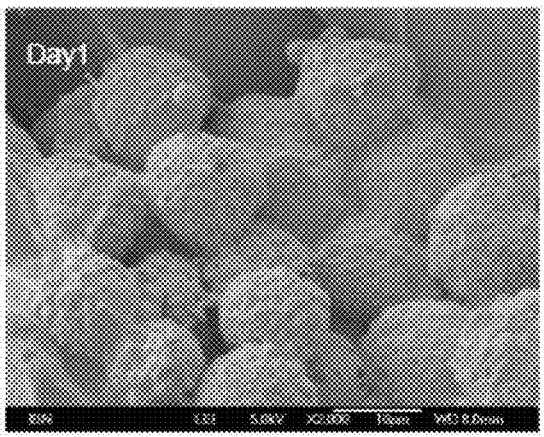
Figure 23:
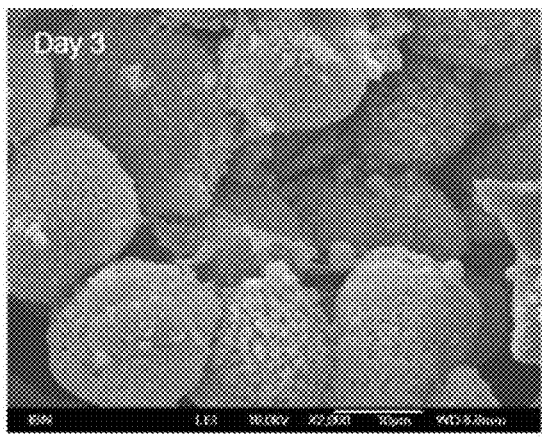
Figure 24:
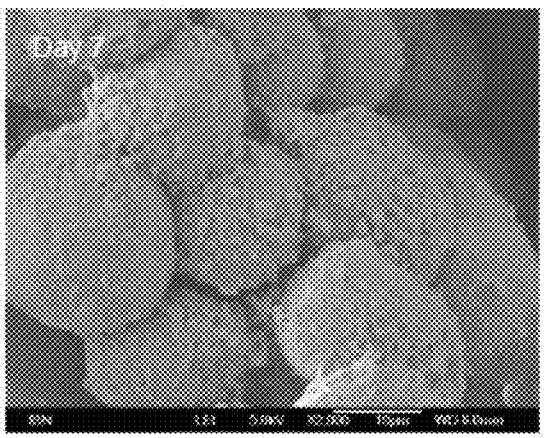

FIGS. 19 and 20 show albulmin secretion and urea synthesis of the primary rat hepatocytes cultured in Sample II, in comparison to 2D collagen monolayer culture. 2D collagen monolayer has been conventionally used for hepatocyte culture. The sustained liver-specific functions of primary rat hepatocytes cultured in the scaffolds were different in the two tested scaffolds. The albumin secretion and urea products of the hepatocytes cultivated in the 3D Sample II were higher than those cultured in the 2D collagen monolayer.

FIGS. 21, 22, 23 and 24 show SEM images of primary rat hepatocytes cultured in Sample II, taken over a period of 7 days, and the morphologies of these cells in Sample II. The cells appeared round and tended to form cellular aggregates in the scaffold, well supported by cell-cell and cell-matrix interactions.

Fluorescence viability staining was also carried out on human MCF-7 breast cancer cells (MCF-7), human hepatoblastoma cells (C3A), showing good cellular biocompatibility.

Figure 25:
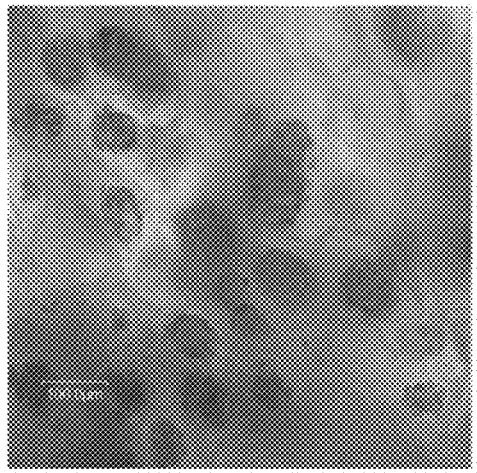
FIG. 25 is a confocal micrograph (transmitted image) of cells cultured in a sample scaffold.
Figure 26:
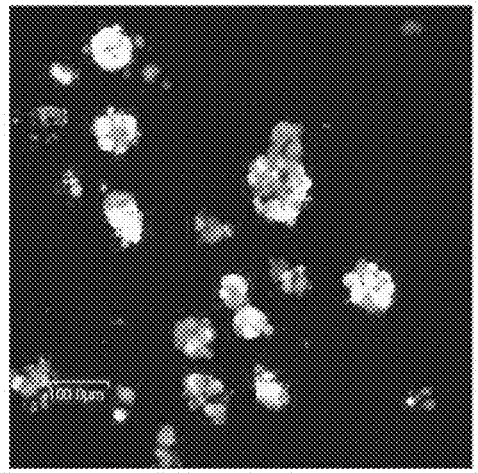
FIG. 26 is a confocal micrograph of the cells cultured in the sample scaffold of FIG. 25.
Figure 27:
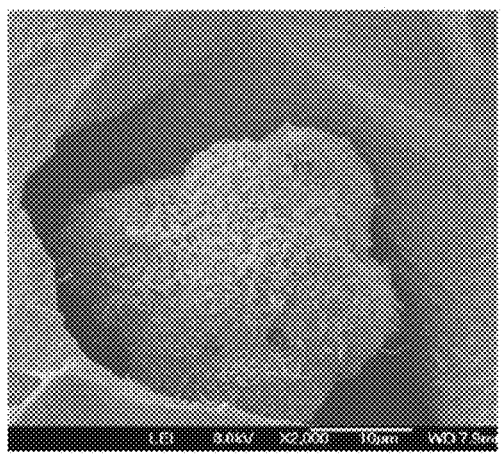
FIG. 27 is an SEM image of the cells cultured in the sample scaffold of FIG. 25 at an earlier time.
Figure 28:
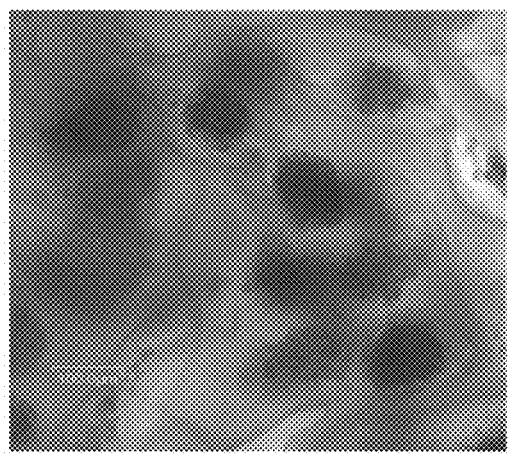
FIG. 28 is a confocal micrograph (transmitted image) of the cells of FIG. 25 at a later time.
Figure 29:
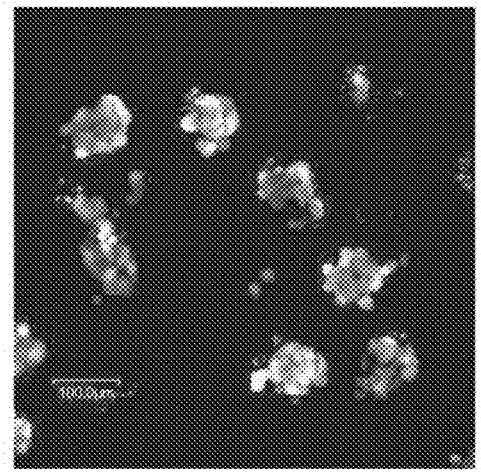
FIG. 29 is a confocal micrograph of the cells of FIG. 28.

FIG. 25 is a transmitted image of C3A cells cultured in sample 3D scaffolds for two days. The C3A cells formed spheroids in the scaffolds. FIG. 26 is a fluorescence image of live/dead staining of the C3A spheroids at day 2. FIG. 27 is an SEM image of the C3A spheroids at day 1 and FIG. 28 is a transmitted image of the C3A spheroids at day 7. FIG. 29 is a fluorescent image of live/dead staining of C3A spheroids at day 7.

Figure 30:
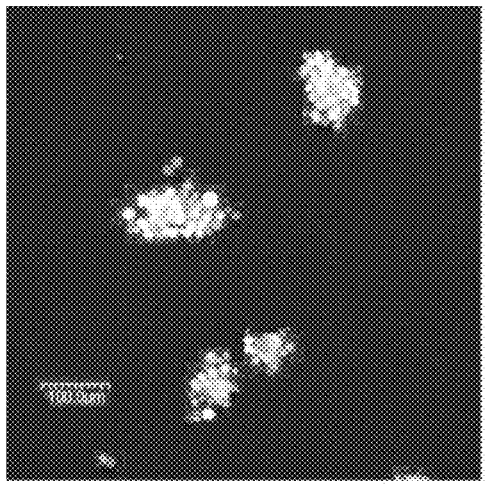
FIGS. 30, 31, 32 and 33 are confocal micrographs of different cells cultured in different sample scaffolds.
Figure 31:
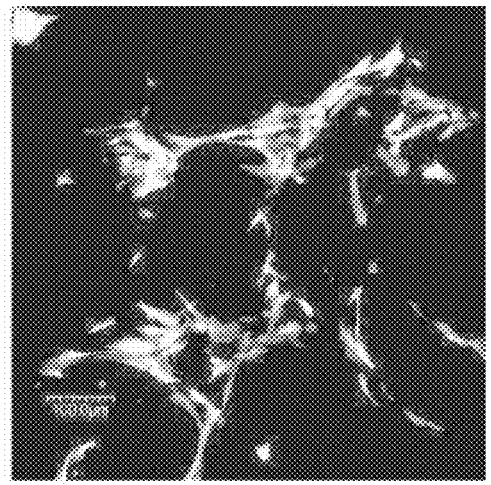
Figure 32:
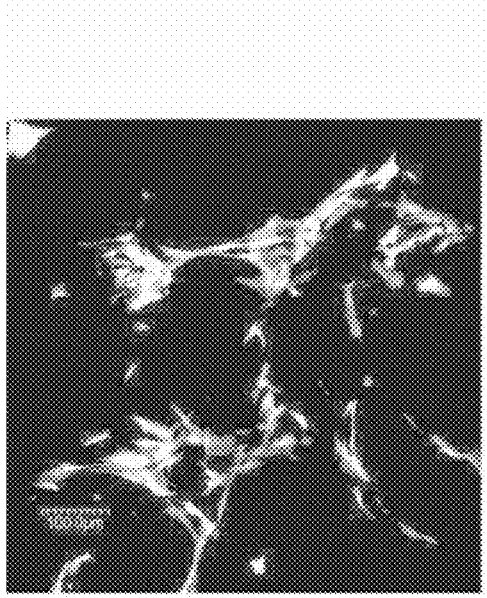
Figure 33:
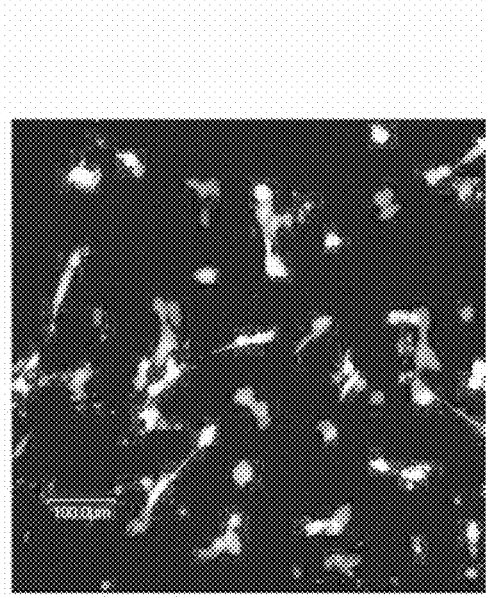

It is expected that the presence of —OH groups in Sample scaffolds can also allow facile incorporation of ECM proteins to improve cell adhesion. This method is also applicable to other types of ECM proteins. Collagen type I was used to verify this expectation. Under sterile condition, scaffolds were rinsed with acetone for three times, then treated with 20 mM 1,1'-carbonyl diimidazole (CDI) overnight at room temperature. It is expected this method is also applicable to other types of ECM proteins. The scaffolds were washed with acetone for 5 times before being immersed into collagen I solution (0.29 mg/ml, pH10.0). The conjugation was conducted on an orbital shaker at 4° C. overnight. The modified scaffolds were then washed with PBS and deionised water before freeze dry. Cell attachment has been significantly improved in the modified scaffolds as demonstrated in FIGS. 31 and 33. in FIG. 30 shows an image of live/dead staining of human foreskin fibroblasts cultured in an unmodified sample scaffold at day 1; FIG. 31 shows an image of live/dead staining of human foreskin fibroblasts cultured in an collagen conjugated sample scaffold at day 1; FIG. 32 shows an image of live/dead staining of human umbilical vein endothelial cells cultured in the unmodified scaffold at day 1; and FIG. 33 shows an image of live/dead staining of human umbilical vein endothelial cells cultured in the collagen conjugated sample scaffold at day 1.

Example VI

Galactosylated Hydroxypropyl Cellulose Scaffold Synthesis and Fabrication

Figure 34:
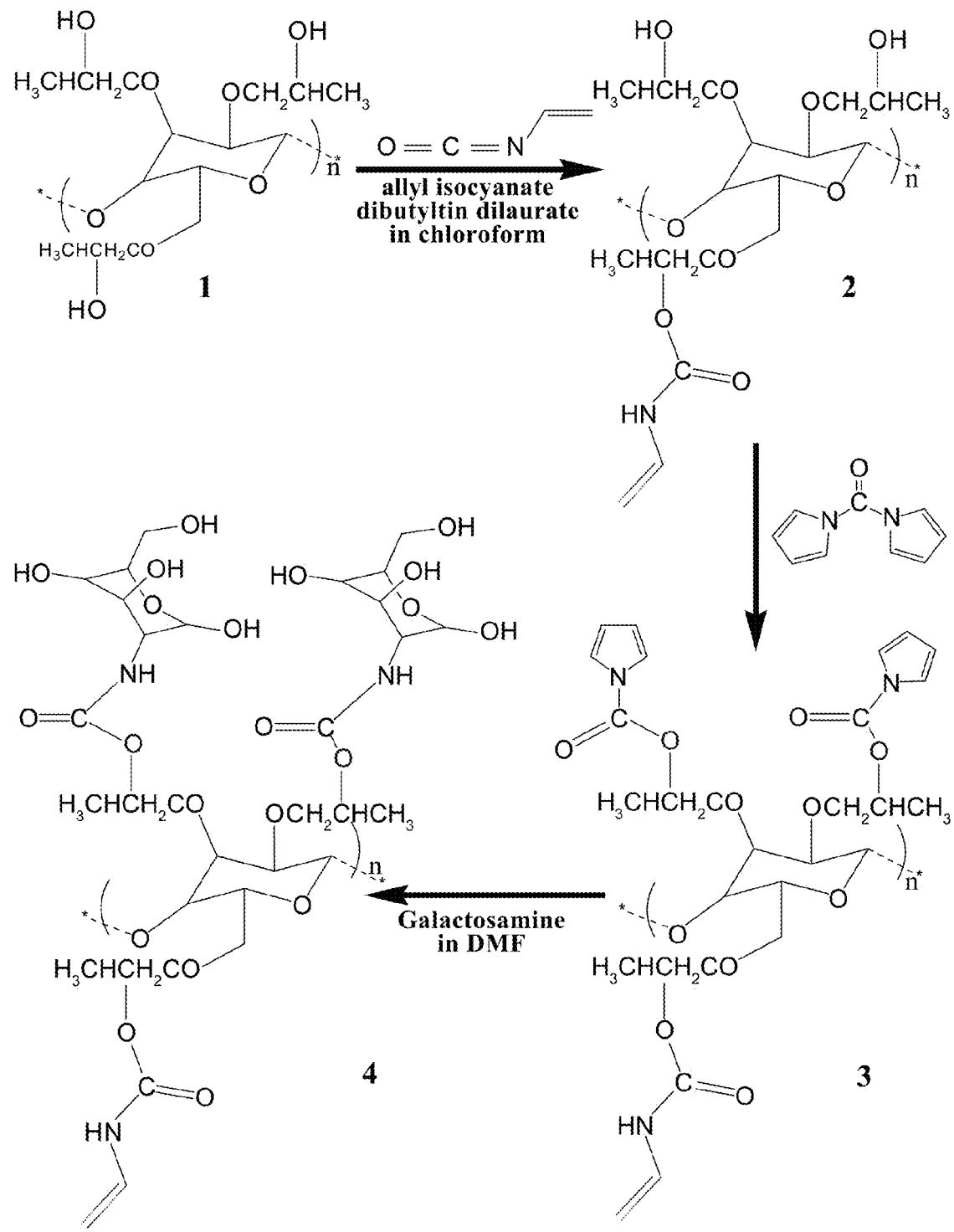
FIG. 34 is a schematic diagram for a synthesis route of a sample scaffold material.

The synthesis procedure of galactosylated hydroxypropyl cellulose (HA Gal) scaffold is illustrated in the schematic diagram of FIG. 34. In FIG. 34, compound 1 is hydroxypropyl cellulose parent molecule, compound 2 is hydroxypropyl cellulose allyl, compound 3 is intermediate molecule of hydroxypropyl cellulose modified with imidazole group, and compound 4 is hydroxypropyl cellulose allyl galactose.

To obtain hydroxypropyl cellulose allyl basic construct, 4 gr of dried hydroxypropyl cellulose (HPC MW 80,000 Da, Sigma Aldrich) was dissolved in 100 ml anhydrous chloroform (Sigma Aldrich™). The mixture was stirred for 1 day at room temperature until completely dissolved. On the next day, 50 ml anhydrous chloroform was added to the mixture to reduce viscosity. 2.095 ml allyl isocyanate 98% (MW 83.04 Da, $\rho$=0.946 g/cm$^3$, Sigma Aldrich) dissolved in 2 ml anhydrous chloroform was added dropwise to the mixture, as a side chain modifier for crosslinking through double bonds. Dibutyltin dilaurate 95% (2 ml, Sigma Aldrich) was added to the mixture as a catalyst. The mixture was stirred for 48 hours at room temperature in sealed flask to prevent moisture. Two days later, the mixture was concentrated in rotary evaporation at 35° C. and precipitated in anhydrous diethyl ether. The fibrous end-product was further vacuum dried for half a day to remove ether traces.

Dialysis was performed in tube with molecular cut off 12 kDa-14 kDa for 3 days in water to remove impurities. The final product was then freeze dried. This product was denoted as HA (hydroxypropyl cellulose allyl).

HA (1 gram) was dissolve in 15 ml anhydrous dimethylformamide. Equimolar of 1,1'-carbonyldiimidazole (CDI, 0.322 g) dissolved in 2 ml anhydrous dimethylformamide was added once the HA had been completely dissolved. Activation of HA hydroxyl groups was performed with CDI for 2 hours at room temperature.

Equimolar of fully dissolved β-D-galactosamine HCl (0.427 g in 30 ml anhydrous dimethylformamide with addition of 500 µl triethylamine as salt-form releaser) was added and reacted for 48 hours. The mixture was then precipitated in excess anhydrous diethyl ether until yellowish slurry was obtained. This slurry was further vacuum dried to remove traces of ether. Dried product was further dissolved in water and dialyzed to remove impurities (dialysis tube with molecular cut off 12 kDa-14 kDa) for 3 days. The product was then freeze dried and kept in desiccators until use.

This product was denoted as HA Gal (hydroxypropyl cellulose allyl galactose).

Figure 35:
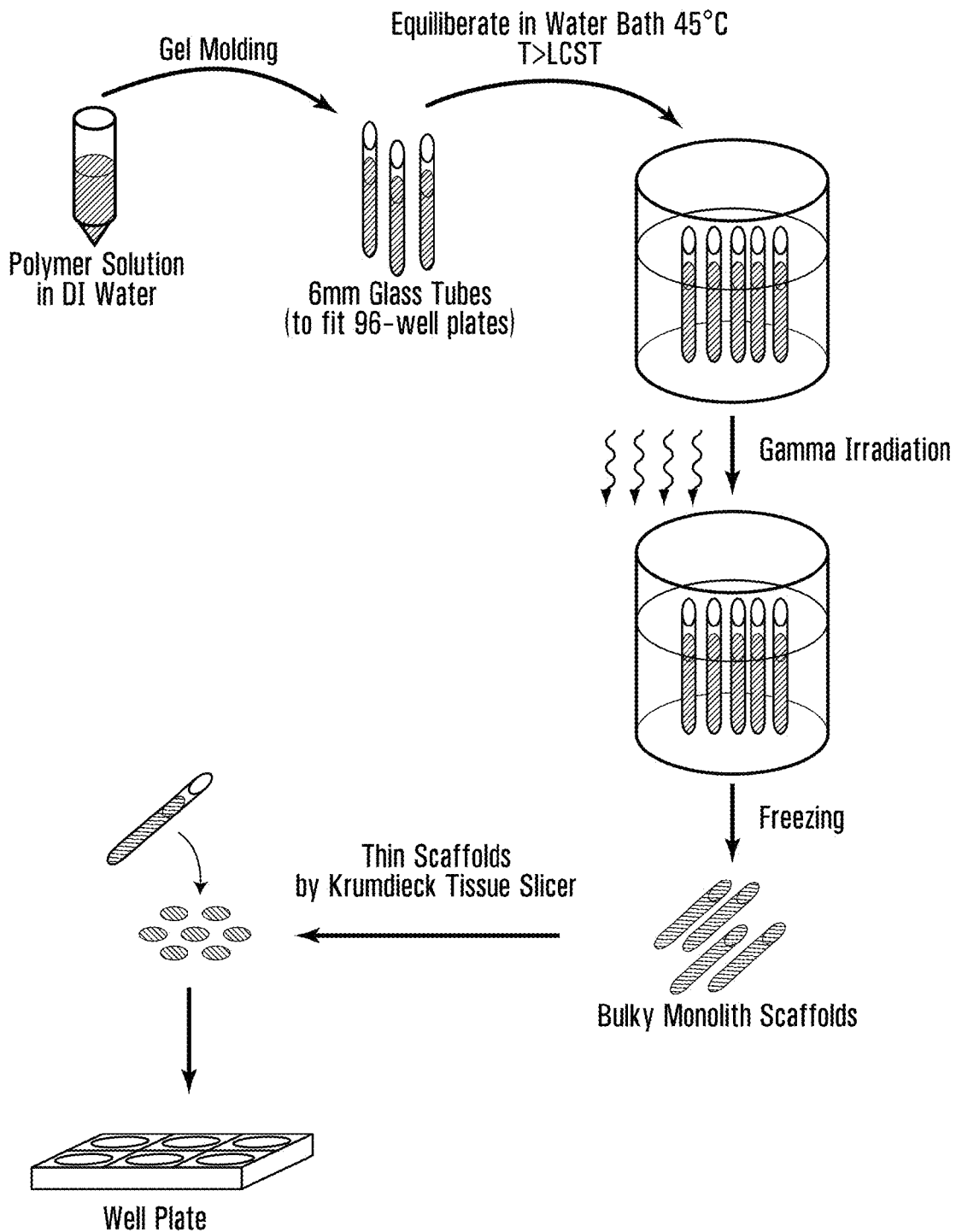
FIG. 35 is a schematic diagram for a process of forming a sample scaffold from the material of FIG. 34.

As schematically illustrated in FIG. 35, purified HA Gal product was dissolved in deonized water at concentration 7.5 wt/vol %. The completely dissolved mixture was poured into small glass tubes (6 mm diameter) at 3 cm height. Bubble-free solution in glass tubes were clustered in bigger vessel and put in 50° C. water bath for 5 min to induce stable colloidal formation. When the solution temperature was increased to above the LCST, phase transition occurred. The clear, transparent solution turned into an opaque colloidal solution at above 45° C. The colloids formed were crosslinked with gamma irradiation for 30 min at 10 kGray/hour. The crosslinked products in the tubes were extracted by breaking the glass tubes at freezing temperature. The products were then sliced evenly at 1 mm thickness in water with Krundieck tissue slicer. These slices were further freeze dried to remove the water and gamma irradiated to sterilize.

The final scaffold products were able to fit 96 well-plates and were ready for cell plating.

Figure 36:
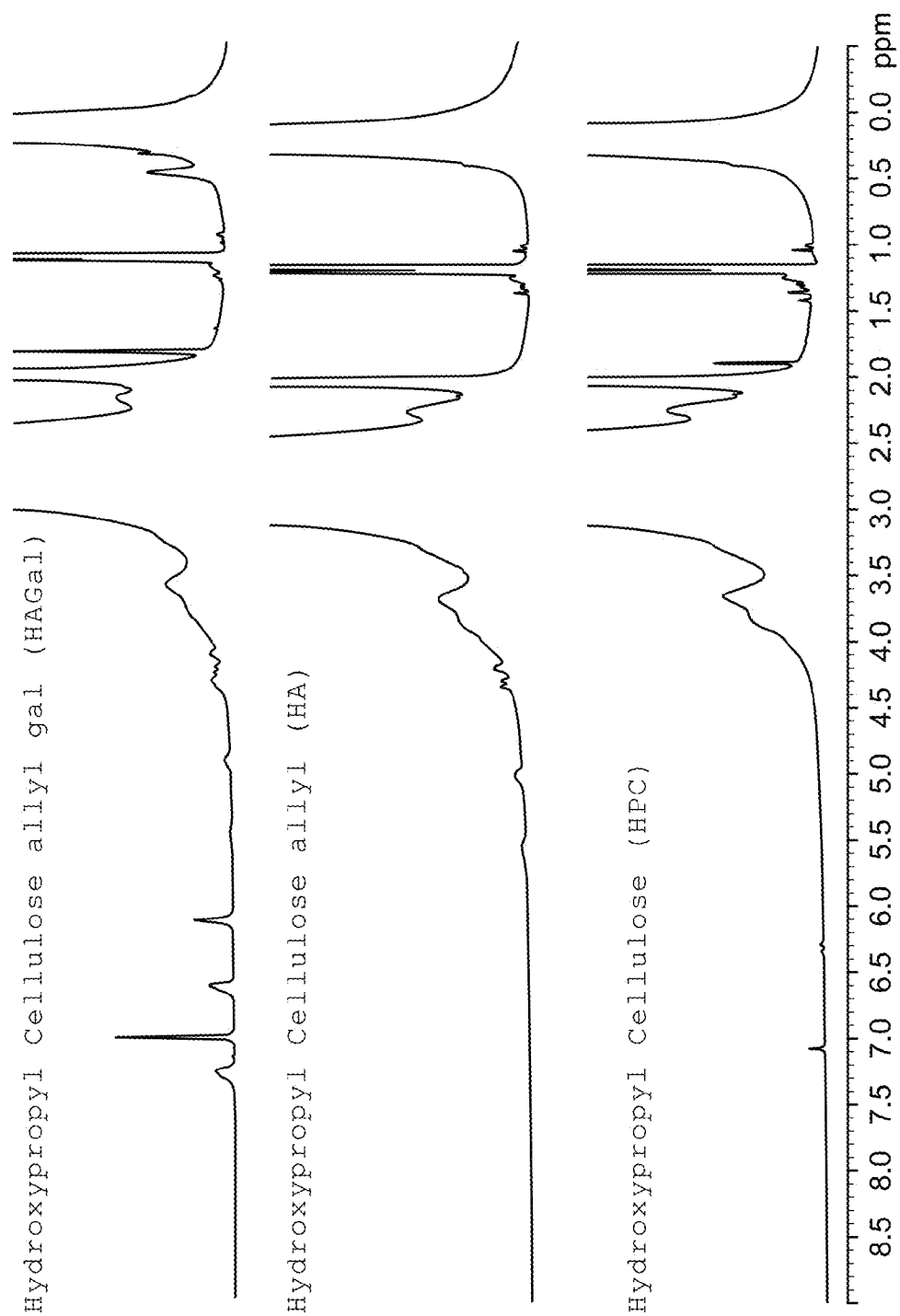
FIG. 36 is a datagraph showing nuclear magnetic resonance (NMR) spectra of different samples.

Representative NMR measurement results of HA Gal, HA and HPC samples are shown in FIG. 36. The NMR spectra of HA Gal show visible peaks around 7 ppm, which indicates formation of amide bond between galactose and hydroxypropyl cellulose through imidazole group. The NMR spectra of HA show visible peaks around 4.5-5 ppm, which indicate existence of allyl group bonds. The bottom NMR spectra in FIG. 35 are for parent molecule hydroxypropyl cellulose (HPC).

Figure 37:
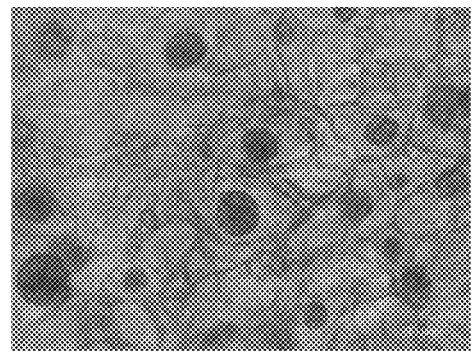
FIGS. 37, 38, 39, and 40 are micrographs of a sample scaffold seeded with cells.
Figure 38:
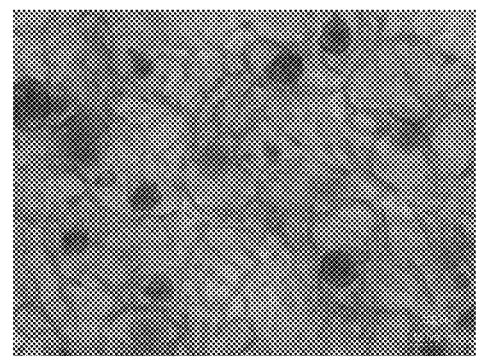
Figure 39:
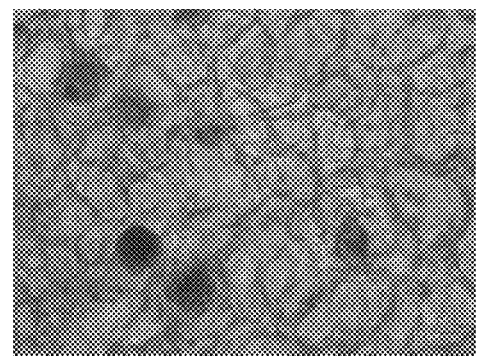
Figure 40:
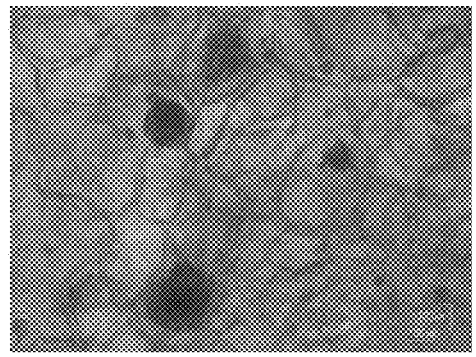

Images of a sample HA Gal scaffold seeded with primary rat hepatocyte were taken at different times after initial seeding. Representative images taken after different seeding periods are shown in FIG. 37 (day 1), FIG. 38 (day 3), FIG. 39 (day 5), and FIG. 40 (day 7). The images show that 3D spheroids were formed as early as 24 hours after initial seeding.

Figure 41:
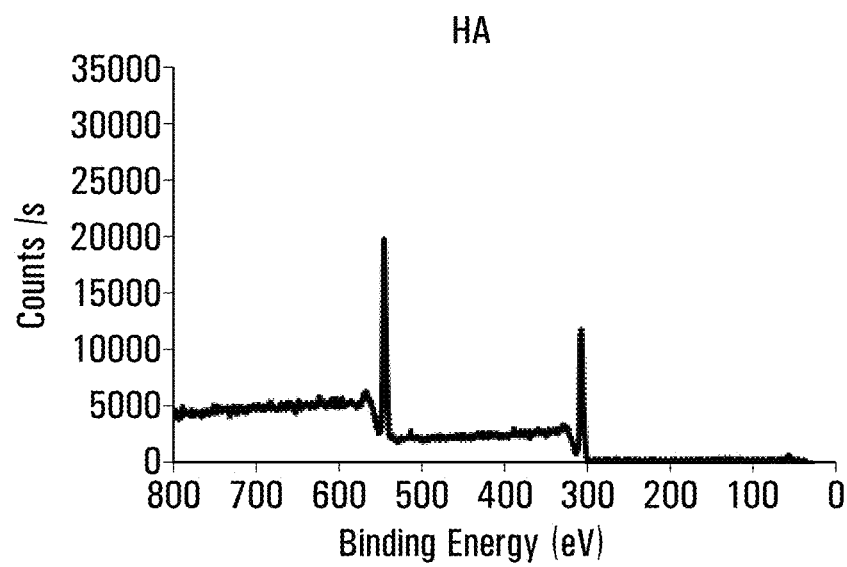
FIGS. 41 and 42 are line graphs showing x-ray photoelectron spectra of different materials.
Figure 42:
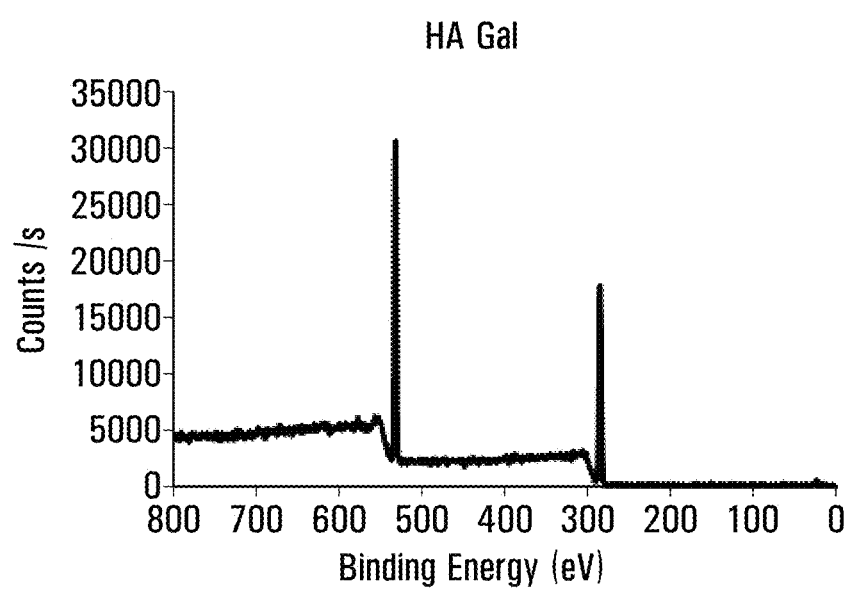

Representative X-ray photonelectron speactra (XPS) of HA and HA Gal are shown in FIGS. 41 (HA) and 42 (HA Gal), respectively. As can be seen, the counts at both 280 eV (Cls) and 550 ev (O) positions are higher for HA Gal than for HA.

Figure 43:
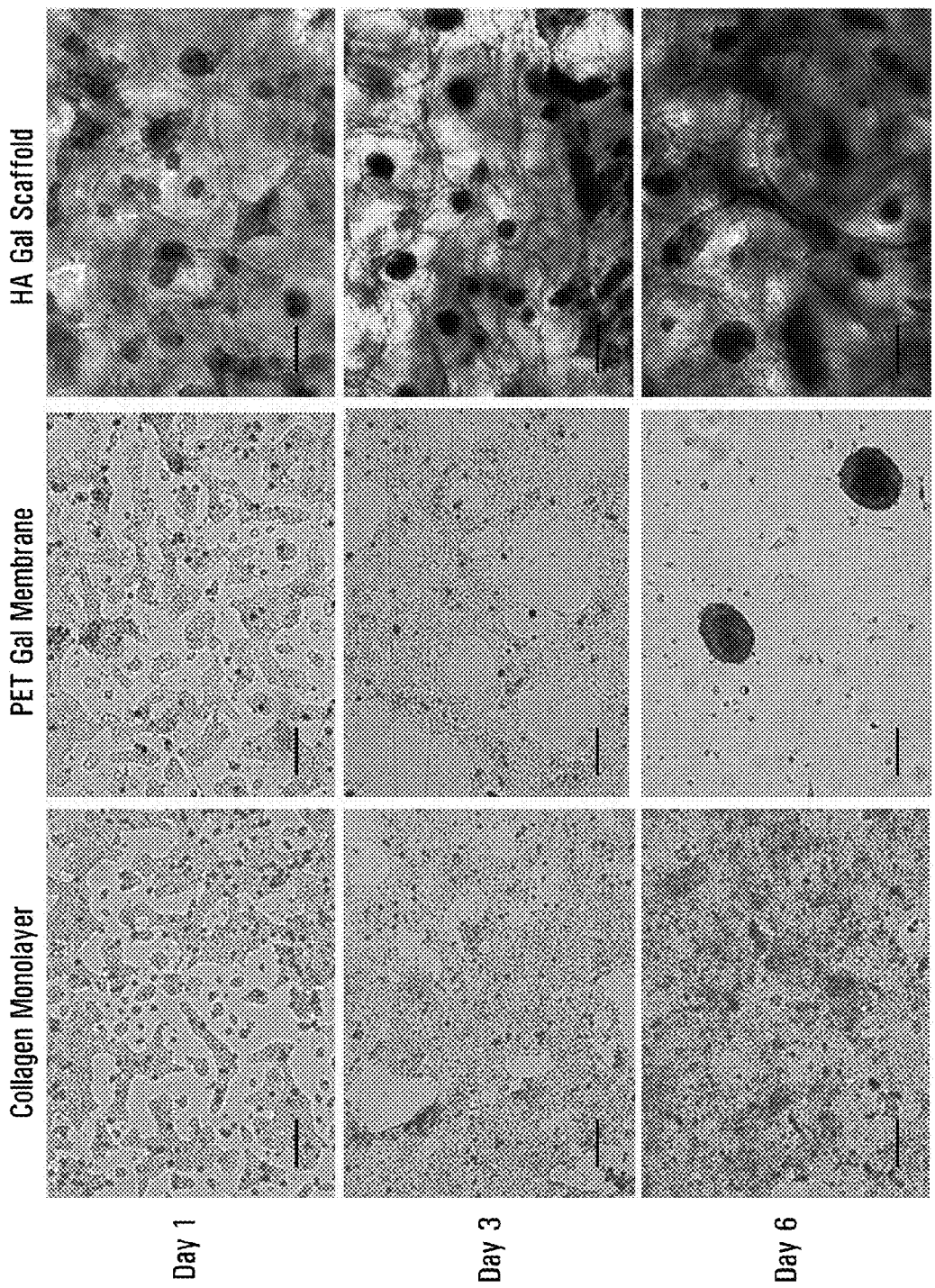
FIG. 43 shows images of cells cultured on different supporting materials.
Figure 45:
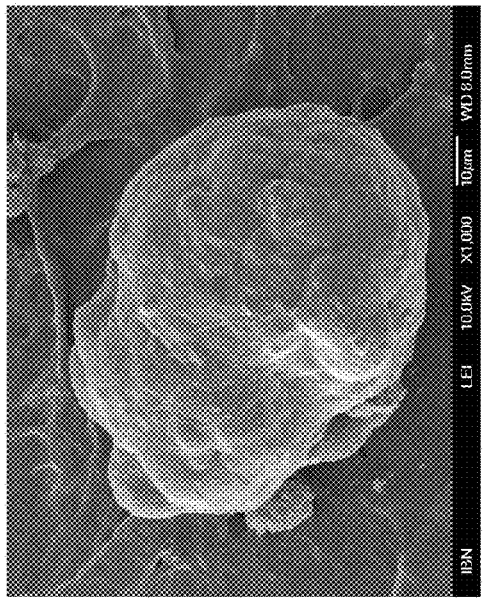
FIGS. 44, 45, 46, and 47 are SEM images of cells on a pore surface of a sample scaffold, exemplary of an embodiment of the present invention.

FIG. 43 compares images of hepatocyte cells cultured on different supporting materials, which were, from the left column to the right column, collagen monolayer, PET Gal membrane, and sample HA Gal scaffold. The images were taken on day 1, 3 or 6 (from top row to bottom row), respectively. The scale bars shown in FIG. 43 represent 60 microns in length. As can be seen, the cells cultured in HA Gal scaffold started to form cell spheroids on day 1. In comparison, visible cell spheroids were formed in PET Gal membrane on after day 3.

Figure 47:
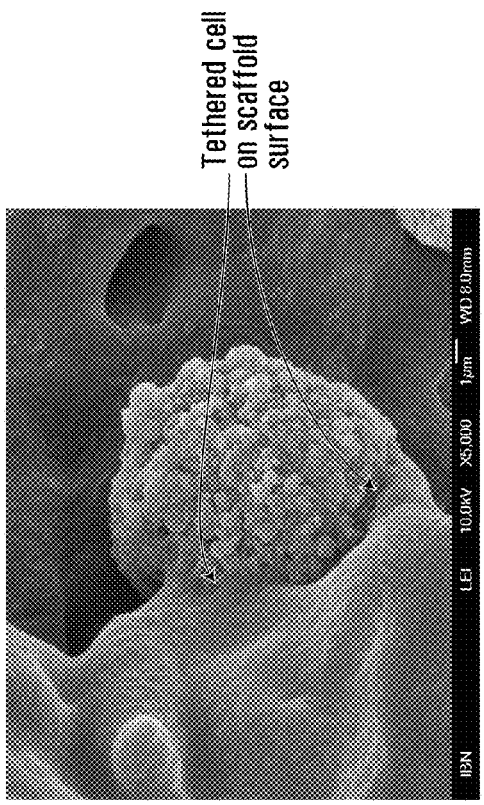
Figure 44:
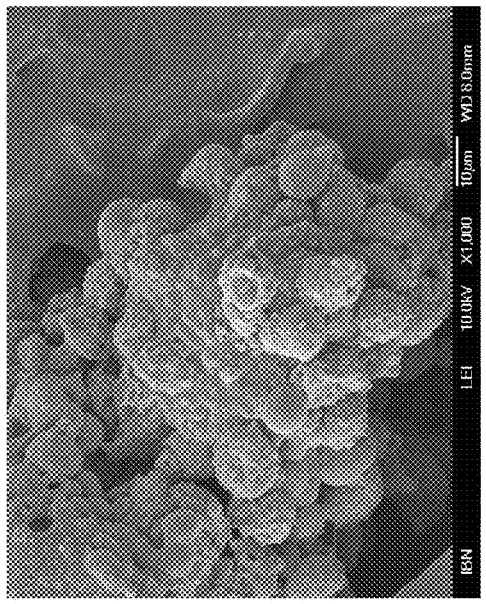
Figure 46:
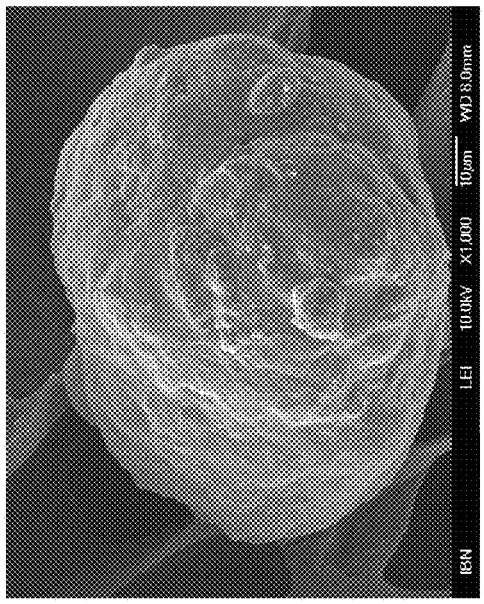
Figure 48:
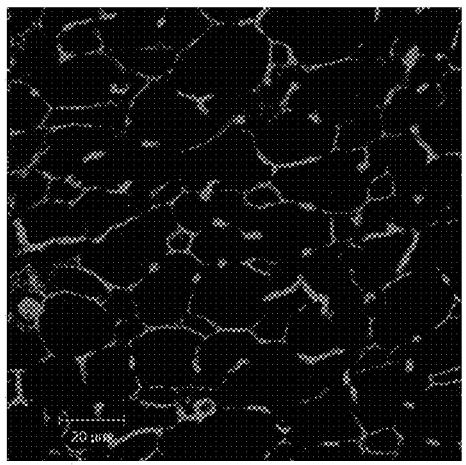
FIGS. 48, 49, 50, 51, and 52 are images of stained cells in a sample scaffold, exemplary on an embodiment of the present invention.
Figure 49:
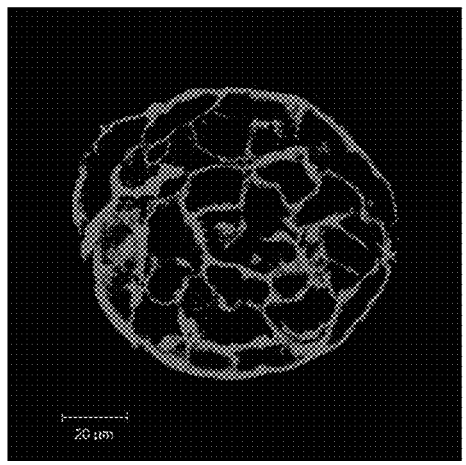
Figure 50:
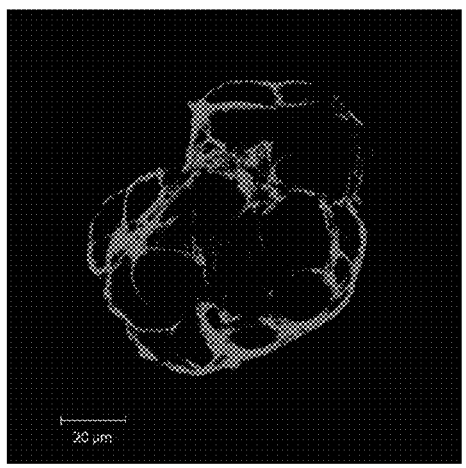
Figure 51:
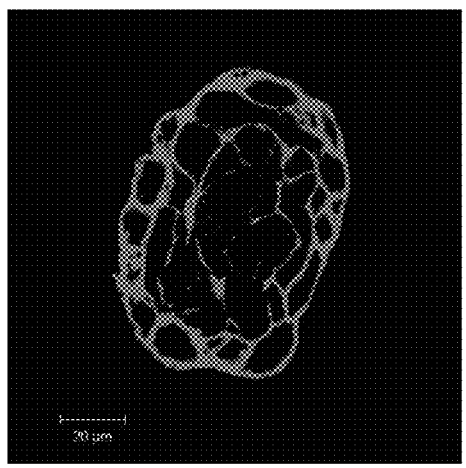
Figure 52:
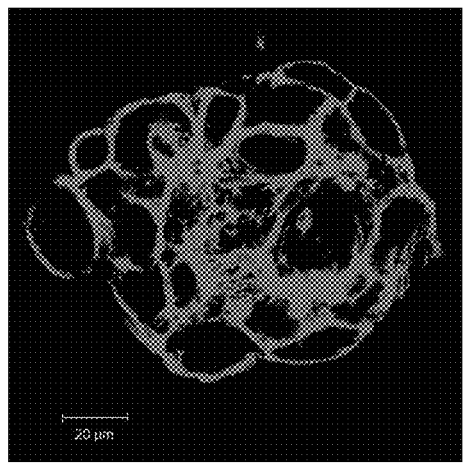

FIGS. 44, 45, 46, and 47 show SEM images of primary rat hepatocytes on the sample HA gal scaffold. Images taken at different times after cell seeding are shown in FIG. 44 (day 1), FIG. 45 (day 3), and FIG. 46 (day 17). FIG. 47 shows a single cell tethered onto the nanoscale surface structure of the sample scaffold.

FIGS. 48, 49, 50, 51, and 52 show images of F-actin stained rat hepatocyte spheroids formed on the sample HA Gal scaffold.

Other features, benefits and advantages of the embodiments described herein not expressly mentioned above can be understood from this description and the drawings by those skilled in the art.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A method of forming a scaffold, comprising:
forming a bicontinuous emulsion comprising a continuous aqueous phase and a continuous polymer phase, said polymer phase comprising hydroxypropylcellulose substituted by a substituent, said substituent comprising a self-crosslinkable group;
crosslinking said substituted hydroxypropylcellulose through said self-crosslinkable group in said bicontinuous emulsion to form a polymer defining interconnected pores, wherein said crosslinking comprises irradiating said emulsion with γ-ray.

2. The method of claim 1, wherein said substituent comprises allyl isocyanate, methacrylic acid, acrylic acid, or glycidyl methacrylate.

3. The method of claim 1, wherein said pores comprise macropores having an average pore size of larger than 50 microns.

4. The method of claim 1, wherein said crosslinking comprises crosslinking at least about 90 wt % of said substituted hydroxypropylcellulose in said emulsion.

5. The method of claim 1, comprising removing water from said pores by freeze-drying said polymer, wherein, after said freeze-drying, said polymer has an interconnected porosity of about 50% or higher, and said pores have an average pore size of larger than 50 microns.

6. The method of claim 1, wherein said emulsion comprises about 80 to about 90 wt % of said aqueous phase and about 10 to about 20 wt % of said polymer phase.

7. The method of claim 1, wherein said substituted hydroxypropylcellulose has a degree of substitution of about 2.5 or less.

8. The method of claim 1, wherein said polymer is a gel.

9. The method of claim 1, wherein said emulsion is formed by subjecting a solution comprising water and said substituted hydroxypropylcellulose to heat treatment at a temperature of about 313 K for about 5 minutes.

10. The method of claim 1, wherein said substituted hydroxypropylcellulose comprises hydroxypropylcellulose allyl galactose, and said method comprises attaching a biocompatible cationic polymeric group to a side chain of said hydroxypropylcellulose allyl galactose, wherein said biocompatible cationic polymeric group comprises polylysine, polyethylene imine, or polypropyleneimine hexadecaamine.

11. The method of claim 1, comprising attaching an arginine-glycine-aspartic acid (RGD), collagen, laminin, fibronectin, or cell growth factor to a surface of said scaffold.

12. A method of forming a scaffold, comprising:
inducing phase separation in a solution comprising a polymer precursor and water,
wherein the polymer precursor comprises a cellulose derivative, to form a bicontinuous emulsion comprising a continuous polymer phase and a continuous aqueous phase, said polymer precursor comprising a self-crosslinkable group; and
crosslinking said polymer precursor through said self-crosslinkable group in said bicontinuous emulsion to form a polymer defining interconnected macropores, wherein said crosslinking comprises irradiating said emulsion with γ-ray.

13. The method of claim 12, wherein said polymer precursor is a cellulose derivative.

14. The method of claim 13, wherein said cellulose derivative is a methylcellulose derivative or a hydroxypropylcellulose derivative, or wherein said cellulose derivative is substituted by a substituent that comprises a self-linkable group.

15. The method of claim 14, wherein said hydroxypropylcellulose derivative is hydroxypropylcellulose substituted by allyl isocyanate, or comprises hydroxypropylcellulose allyl galactose.

16. The method of claim 14, wherein said substituent comprises allyl isocyanate, methacrylic acid, acrylic acid, or glycidyl methacrylate.

17. The method of claim 12, wherein said self-crosslinkable group comprises an unsaturated double carbon-carbon bond.

18. The method of claim 12, wherein
said polymer precursor is thermo-sensitive, and said inducing phase separation comprises heating said solution; or
said polymer precursor is pH-sensitive, and said inducing phase separation comprises changing pH of said solution.

19. The method of claim 12, wherein said polymer is a gel.

* * * * *